United States Patent
Hernandez et al.

(10) Patent No.: US 11,724,115 B2
(45) Date of Patent: Aug. 15, 2023

(54) SYSTEM AND METHOD FOR REDUCING HEAT OF AN IMPLANTABLE MEDICAL DEVICE DURING WIRELESS CHARGING

(71) Applicant: Advanced Neuromodulation Systems Inc., Plano, TX (US)

(72) Inventors: Luis Ortiz Hernandez, Plano, TX (US); Li Sun, Plano, TX (US); Nicholas Sachs, Plano, TX (US)

(73) Assignee: Advanced Neuromodulation Systems Inc., Plano, TX (US)

( * ) Notice: Subject to any disclaimer, the term of this patent is extended or adjusted under 35 U.S.C. 154(b) by 48 days.

(21) Appl. No.: 17/170,473

(22) Filed: Feb. 8, 2021

(65) Prior Publication Data

US 2022/0203104 A1  Jun. 30, 2022

Related U.S. Application Data

(60) Provisional application No. 63/132,061, filed on Dec. 30, 2020.

(51) Int. Cl.
| | | |
|---|---|---|
| *A61N 1/36* | (2006.01) | |
| *A61N 1/378* | (2006.01) | |
| *A61N 1/372* | (2006.01) | |
| *A61N 1/08* | (2006.01) | |

(52) U.S. Cl.
CPC .......... *A61N 1/3787* (2013.01); *A61N 1/08* (2013.01); *A61N 1/36142* (2013.01); *A61N 1/37247* (2013.01)

(58) Field of Classification Search
CPC .... A61N 1/3787; A61N 1/08; A61N 1/36142; A61N 1/37247
See application file for complete search history.

(56) References Cited

U.S. PATENT DOCUMENTS

| | | | |
|---|---|---|---|
| 5,411,537 A | 5/1995 | Munshi et al. | |
| 5,702,431 A | 12/1997 | Wang et al. | |
| 8,731,682 B2 | 5/2014 | Winstrom | |
| 8,818,523 B2 | 8/2014 | Olson et al. | |
| 8,880,184 B2 | 11/2014 | Phillips et al. | |
| 9,209,634 B2 | 12/2015 | Cottrill et al. | |
| 9,270,134 B2 | 2/2016 | Gaddam et al. | |
| 9,339,660 B2 | 5/2016 | Feldman et al. | |
| 10,682,520 B2 | 6/2020 | Kelly et al. | |
| 2005/0245996 A1* | 11/2005 | Phillips ................ | A61N 1/3787 607/61 |
| 2005/0288739 A1 | 12/2005 | Hassler et al. | |

(Continued)

*Primary Examiner* — Eugene T Wu
(74) *Attorney, Agent, or Firm* — Jessica W. Smith; Loza & Loza, LLP

(57) ABSTRACT

A wireless charger device is configured to charge an implantable medical device (IMD). A patient controller obtains one or more power parameters from the charger device during charging of the IMD. The patient controller estimates a temperature range of the IMD using the one or more power parameters from the charger device and compares to a heating threshold. The patient controller then determines whether one or more spacers are recommended in response to the comparison. The one or more spacers are removably attached to the wireless charger device and are configured to lay in a position between the wireless charger device and a patient's skin to increase a charging path.

20 Claims, 14 Drawing Sheets

(56) References Cited

U.S. PATENT DOCUMENTS

| | | | |
|---|---|---|---|
| 2012/0012630 A1* | 1/2012 | Lui | A41F 9/002 224/660 |
| 2013/0193914 A1* | 8/2013 | Gaddam | H02J 7/007 320/108 |
| 2017/0209705 A1* | 7/2017 | Faltys | A61N 1/3787 |
| 2018/0126177 A1* | 5/2018 | Scott | A61F 7/0085 |
| 2020/0324126 A1 | 10/2020 | Winstrom | |
| 2022/0134116 A1* | 5/2022 | Fried | G01K 7/427 607/116 |

* cited by examiner

SYSTEM AND METHOD FOR REDUCING HEAT OF AN IMPLANTABLE MEDICAL DEVICE DURING WIRELESS CHARGING

CROSS REFERENCE TO RELATED APPLICATIONS

This application claims priority under 35 U.S.C. § 119 to U.S. Provisional Application No. 63/132,061 entitled, "SYSTEM AND METHOD FOR REDUCING HEAT OF AN IMPLANTABLE MEDICAL DEVICE DURING WIRELESS CHARGING," filed Dec. 30, 2020, and hereby expressly incorporated by reference herein.

FIELD

The present disclosure relates generally to providing an external source of energy to an implantable medical device and more particularly, to a system and method for reducing heat in the implantable medical device during wireless charging of the rechargeable battery or during provision of energy to a battery-less implantable medical device.

BACKGROUND

The statements in this section provide a description of related art and are not admissions of prior art. No admission is made that the related art is publicly available or known to others besides the inventors.

An implantable medical device (IMD) is partially or totally introduced, surgically or medically, into the body of a patient, human or non-human. An IMD includes for example, a neurostimulation device for spinal cord stimulation, deep brain stimulation, cortical stimulation, cochlear nerve stimulation, peripheral nerve stimulation, vagal nerve stimulation, sacral nerve stimulation, and others. For example, the IMD may be a spinal cord stimulator (SCS) that treats chronic pain by delivering stimulation pulses to a patient's spinal cord to induce paresthesia in regions of the patient's body. Other examples of IMDs include pacemakers for treating cardiac arrhythmia, defibrillators for treating cardiac fibrillation, cochlear stimulators for treating deafness, retinal stimulators for treating blindness, or muscle stimulators for producing coordinated limb movement or reducing tremors. In addition, IMDs may include any other device configured for implantation in a patient.

An electrically operated IMD implanted in the patient needs a reliable power source. Some electrically operated IMDs are powered by a primary cell (commonly referred to as a non-rechargeable battery). When the battery of such an IMD is depleted, the device must be removed from the patient's body so that its battery can be replaced or a new IMD with a new battery may be implanted. To avoid surgery and removal of an IMD, other electrically operated IMDs include secondary cells (commonly referred to as rechargeable batteries). The rechargeable battery of such an IMD is recharged using a non-implanted or external wireless charger device. For example, the external charger device includes an inductive coil that enables power to be wirelessly transferred, through the patient's skin, from the charger device to an inductive coil in the IMD to charge the rechargeable battery. In another embodiment, the IMD has no internal power source and is powered by an external wireless source. The charger device transfers power to an inductive coil in the IMD to power the IMD wirelessly.

In general, to effectively recharge the IMD, the external charger device should be positioned over the skin of the patient and within a certain range and alignment of the IMD. One of the biggest challenges of wirelessly charging the IMD is the unwanted heat generated during charging. The IMD may contain metal for its casing and when using wireless charging, it generates eddy currents on metal components in the charging path. Without an effective heat dissipation path, the eddy currents may accumulate heat locally and become a source of unwanted heat. This heat can cause effects from a slightly uncomfortable sensation to severe tissue damage.

Thus, there is a need for an improved system and method for reducing heat while wirelessly charging an IMD. Other advantages of embodiments of the systems and methods are described herein or are apparent from implementations thereof.

SUMMARY

The following presents a summary of the disclosed subject matter in order to present some aspects of the disclosed subject matter.

In one aspect, an external device includes a transceiver configured to communicate with a wireless charger device, wherein the wireless charger device is configured to charge an implantable medical device (IMD). The external device also includes at least one processing circuit having at least one processing device and at least one memory device, wherein the at least one memory device stores instructions that, when executed by the at least one processing device, causes the external device to: obtain one or more power parameters from the charger device and estimate a temperature range of the IMD using the one or more power parameters from the charger device.

In a second aspect, an external device includes a transceiver configured to communicate with an implantable medical device (IMD), wherein the wireless charger device is configured to charge the IMD. The external device also includes at least one processing circuit including at least one processing device and at least one memory device, wherein the at least one memory device stores instructions that, when executed by the at least one processing device, causes the external device to obtain at least one temperature measurement from the IMD at each of a plurality of periodic intervals; compare the at least one temperature measurement at each of the plurality of periodic intervals to one or more heat thresholds; and when the at least one temperature measurement at one or more of the plurality of periodic intervals exceeds one or more of the heating thresholds, determine to recommend an implementation of at least one spacer, wherein the at least one spacer includes a fastener to couple the at least spacer to the charger device and position the at least one spacer on a charging pad of the charger device.

In a third aspect, a method of an external device, wherein the external device controls at least one implantable medical device (IMD), includes obtaining one or more power parameters from a wireless charger device, wherein the one or more power parameters are obtained when the wireless charger device is charging the IMD and estimating a temperature range of the IMD using the one or more power parameters from the charger device.

In one or more of the above aspects, the external device compares the temperature range of the IMD to a heating threshold. When the temperature range of the IMD exceeds the heating threshold, the external device determines to recommend coupling at least one spacer to the charger device, wherein the at least one spacer is removably coupled to the charger device in a position to lay adjacent to a charging pad of the charger device and face the patient's skin.

In one or more of the above aspects, the external device determines to a depth of the at least one spacer in response to the comparison of the temperature range of the IMD and the heating threshold.

In one or more of the above aspects, the external device determines to recommend the depth of the at least one spacer in response to a percentage that the temperature range of the IMD exceeds the heating threshold.

In one or more of the above aspects, when the temperature range of the IMD is within the heating threshold, the external device generates an indication to a user that a spacer is optional.

In one or more of the above aspects, the one or more power parameters obtained from the charger device include one or more of: a bridge current, a bridge voltage or a phase difference between the bridge current and the bridge voltage.

In one or more of the above aspects, the external device determines a depth of the at least one spacer. The external device may determine to recommend the depth of the at least one spacer in response to a percentage that the temperature of the IMD exceeds the heating threshold.

In one or more of the above aspects, the external device obtains one or more power parameters from the IMD and determines a depth of the at least one spacer using the one or more power parameters from the charger device and IMD.

In one or more of the above aspects, the external device generates an indication to a user that a spacer is optional.

In one or more of the above aspects, the external device determines the temperature range of the IMD using a predetermined correlation, wherein the predetermined correlation associates the one or more parameters to a temperature of the IMD.

Additional aspects are set forth, in part, in the detailed description, figures and claims which follow, and in part may be derived from the detailed description, or may be understood by practice of the embodiments. It is to be understood that the description herein is exemplary and explanatory only and is not restrictive of the embodiments as claimed.

BRIEF DESCRIPTION OF THE DRAWINGS

The present disclosure may be better understood, and its numerous features and advantages made apparent to those skilled in the art by referencing the accompanying drawings. The use of the same reference symbols in different drawings may indicate similar, equivalent, or identical components or a different embodiment of a component.

DETAILED DESCRIPTION

The description and drawings merely illustrate the principles of various embodiments. Additional arrangements, although not explicitly described or shown herein, are intended to be included within a scope of the disclosure. Furthermore, examples recited herein are intended for pedagogical purposes to aid in understanding the principles of the embodiments and are not intended to limit the scope to such specifically recited examples. Moreover, statements herein reciting principles, aspects, and embodiments, as well as specific examples thereof, are intended to encompass equivalents thereof.

Figure 1A:
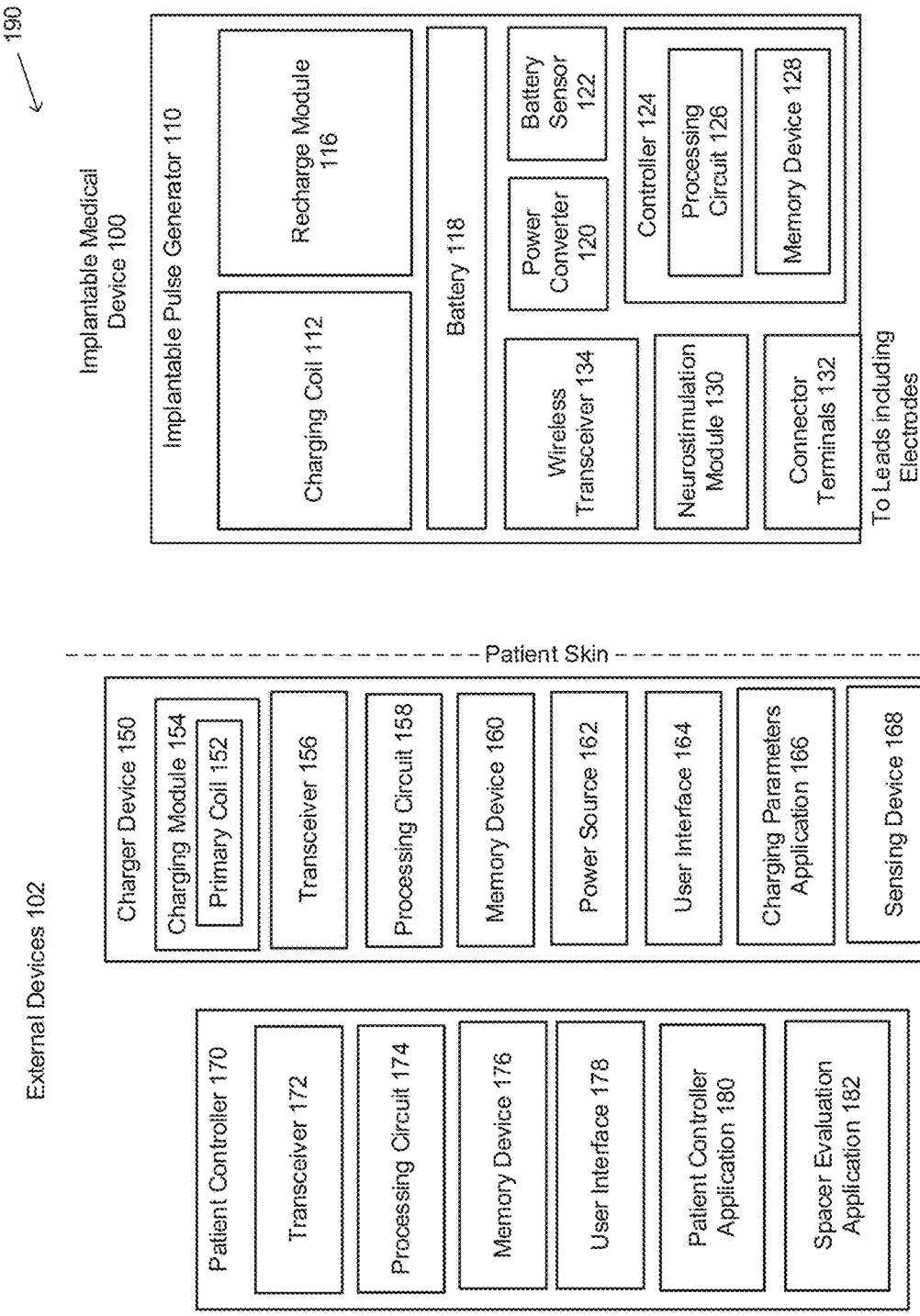
FIG. 1A is a schematic block diagram illustrating an embodiment of selected components of an implantable medical device (IMD) and external devices according to some embodiments.

FIG. 1A is a schematic block diagram illustrating an embodiment of selected components of an implantable medical device (IMD) 100 and external devices 102. The system 190 in FIG. 1A is intended to be exemplary, and in other implementations may include additional or alternative components or devices. In this example, the IMD 100 is an implantable pulse generator (IPG) 110 configured for spinal cord stimulation or deep brain stimulation, though a person of skill in the art will understand that other types of IMDs may also implement the embodiments herein. The IMD 100 is implanted under the patient's skin and is internal to the patient or user, human or non-human. The IMD 100 is generally implanted subcutaneously at depths, depending upon the application and patient, from 5 mm to 25 mm where there is sufficient tissue to support the implanted system.

The IPG 110 in this example includes a charging coil 112, a recharge module 116, battery 118, power converter 120 and battery sensor 122. The battery 118 is a rechargeable battery such as a lithium ion battery, but is not limited thereto. The recharge module 116 is operable to receive externally generated power through the charging coil 112, and uses the externally generated power to charge the battery 118. The power convertor 120 converts power from the battery 118 for transfer to one or more components of the IPG 110. The battery sensor 122 determines a power level of the battery 118 and provides alerts when the battery 118 is fully charged or when the battery 118 is low on power.

A controller 124 includes at least one processing circuit 126 and at least one memory device 128 and is configured to control the one or more functions of the IPG 110 described herein. The memory device 128 is a non-transitory, processor readable medium that stores programs, code, states, instructions and/or data which when executed or processed by the processing circuit 126, causes the IPG 110 to perform one or more functions described herein.

The IPG 110 further includes a neurostimulation module 130 configured to generate electrical pulses for delivery by electrodes to target neural tissue. The IPG 110 is coupled to the electrodes via one or more leads. The connector terminals 132 couple the leads to the IPG 110. The neurostimulation module 130 delivers electrical pulses in accordance with selected neurostimulation parameters, which can specify a lead, an electrode configuration for the specified lead, and one or more pulse parameters, including, but not limited to, pulse amplitude, pulse width and pulse repetition rate parameters.

In an embodiment, the IPG 110 communicates with the charger device 150 using near field communication, such as reflected impedance modulation, which is sometimes known in the art as Load Shift Keying (LSK) or Amplitude-shift keying (ASK). LSK, which is a particular form of ASK, is a communication scheme that allows simultaneous powering and data transmission through inductive coupling, e.g. of the charging coil 112 with a primary coil 152 of the external charger device 150. A change of the load on the charging coil 112 is reflected onto the primary coil 152 as a varying impedance (i.e., reflected impedance). A near field communication protocol is used to communicate information to the charger device 150 during charging. For example, the IPG 110 communicates that charging is initiated, the battery 118 is fully charged, or charging has halted.

In this embodiment, a wireless transceiver 134 in the IPG 110 is configured to communicate with a patient controller using a proprietary wireless protocol or a standard wireless protocol, e.g. such as the wireless Bluetooth™ protocol standard. The wireless transceiver 134 may additionally or alternatively use a wireless far field communication protocol with one or more of the external devices 102, e.g. such as the Medical Implant Communication Service (MICS) standard, which was defined by the U.S. Federal Communications Commission (FCC) and European Telecommunications Standards Institute (ETSI). The MICS standard uses the RF band between 402 and 405 MHz to provide for bi-directional radio communication with implantable medical devices (IMDs), such as the IPG 110. In 2009 the FCC began referring to the RF band between 402 and 405 MHz as being part of the 401 to 406 MHz Medical Device Radio communications (MedRadio) Service band. Accordingly, the RF band between 402 and 405 MHz can be referred to as the MICS/MedRadio band, and the communication standards relating to the MICS/MedRadio band can be referred to as the MICS/MedRadio communication standards. Alternatively, the wireless transceiver 134 can perform wireless RF communications with one or more of the external devices 102 using the Industrial, Scientific, and Medical (ISM) radio bands. The IPG 110 may also perform wireless communication with one or more of the external devices 102 using the 3GPP Release 13, eMTC, NB-IOT or EC-GSM-IoT standards, and in particular the Internet of Medical Things (IoMT) applications of such standards. The use of other standards and frequency bands are also possible.

The IPG 110 typically includes at least one printed circuit board (PCB) with the above various electronic components mounted to the at least one PCB. The one or more PCBs may include the charging coil 112 as well as a second coil for use as an antenna for the wireless transceiver 134. In another embodiment, the charging coil 112 may be wrapped around the PCB including one or more of these components. The various components may be coupled either directly or indirectly via separate buses or via a shared data bus.

The external devices 102 are non-implanted or non-implantable devices and are external to the skin of the patient. The external devices 102 in this example of the system 190 include a charger device 150 and a patient controller 170. The patient controller 170 may be a dedicated control device or a non-dedicated user device, such as a smart phone, smart tablet, smart watch, laptop, desktop, or any other external control device configured to control the IPG 110. The patient controller 170 includes a transceiver 172 that is configured to communicate at least with the wireless transceiver 134 of the IPG 110 and with the charger device 150, using one or more wireless communication protocols, e.g. such as described herein with respect to the wireless transceiver 134 of the IPG 110.

The patient controller further includes a processing circuit 174, a memory device 176, and a user interface 178. The user interface 178 may include one or more of a display, keyboard, touchscreen, touchpad, mouse or other such input or output devices. The memory device 176 is a non-transitory, processor readable medium that stores programs, code, states, instructions and/or data which when executed or processed by the processing circuit 174, causes the patient controller 170 to perform one or more functions described herein.

A patient controller application 180 is configured to adjust parameters of the IPG 110 in accordance with a patient's prescribed program. For example, the patient may control a mode of the IPG 110 (Airplane Ready Mode, Surgery Mode or MRI Mode) or a type of therapy program (continuous, intermittent or sleep) or a strength of the stimulation pulses. The patient controller 170 receives the control commands from the patient through the user interface 178 and transmits the control commands to the IPG 110.

In an embodiment, the patient controller 170 further includes a spacer evaluation application 182. The spacer evaluation application 182 may be implemented as a component or function of the patient controller application 180 or be implemented as a separate application. The spacer evaluation application 182 determines whether one or more spacers need to be positioned between the charger device 150 and the patient's skin as described in more detail hereinbelow.

The charger device 150 includes a transceiver 156, processing circuit 158, memory device 160, power source 162 and user interface 164. The transceiver 156 is configured to communicate with the transceiver 172 of the patient controller, e.g. such as described hereinabove. The memory device 160 is a non-transitory, processor readable medium that stores programs, code, states, instructions and/or data which when executed or processed by the processing circuit 158 enables the charger device 150 to perform one or more functions described herein. The user interface 164 includes one or more of a display, keyboard, touchscreen, touchpad, mouse or other such input or output devices. The user interface 164 allows a patient or clinician to operate the charger device 150.

The charger device 150 further includes a charging module 154 including a primary coil 152 configured for power transmission to the charging coil 112 of the IPG 110. Power transmission from the charger device 150 to the IPG 110 occurs wirelessly and transcutaneously through the patient's skin and tissue, via inductive coupling. Such an inductive coupling enables the IPG 110 to receive power from the charger device 150 and recharge its battery 118. More specifically, an alternating current (AC) in the primary coil 152 generates a magnetic field with a fluctuating magnetic field strength. This fluctuating magnetic field in turn induces an AC current in the charging coil 112. The AC current is rectified and smoothed by the recharge module 116 to output a substantially constant DC voltage signal. This substantially constant DC voltage signal is then applied to charge or recharge the battery 118.

In an embodiment, as described above, the charger device 150 may communicate with the IPG 110 through inductive coupling, e.g. of the primary coil 152 of the external charger device 150 with the charging coil 112 of the IPG 110. The charger device 150 and IMD 100 may use a near field communication protocol, such as the Wireless Power Consortium (WPC) Qi wireless charging standard, Version 1.2.4 released in 2017 or other standard or proprietary protocol for communication using inductive coupling.

In an embodiment, a power parameters application 166 collects at least one or more power parameters from the charging module 154. A sensing circuit 168 may include one or more sensors, such as a voltmeter or multimeter, that detects the power parameters. The power parameters may include voltage, current or impedance measurements detected from the charging module 154 and/or primary coil 152, such as a bridge current, a bridge voltage or a phase difference between the bridge current and the bridge voltage. The charger device 150 communicates the detected power parameters to the patient controller 170. The patient controller 170 uses the power parameters to determine whether one or more spacers need to be positioned between the charger device 150 and the patient's skin to reduce heating as described in more detail herein.

Figure 1B:
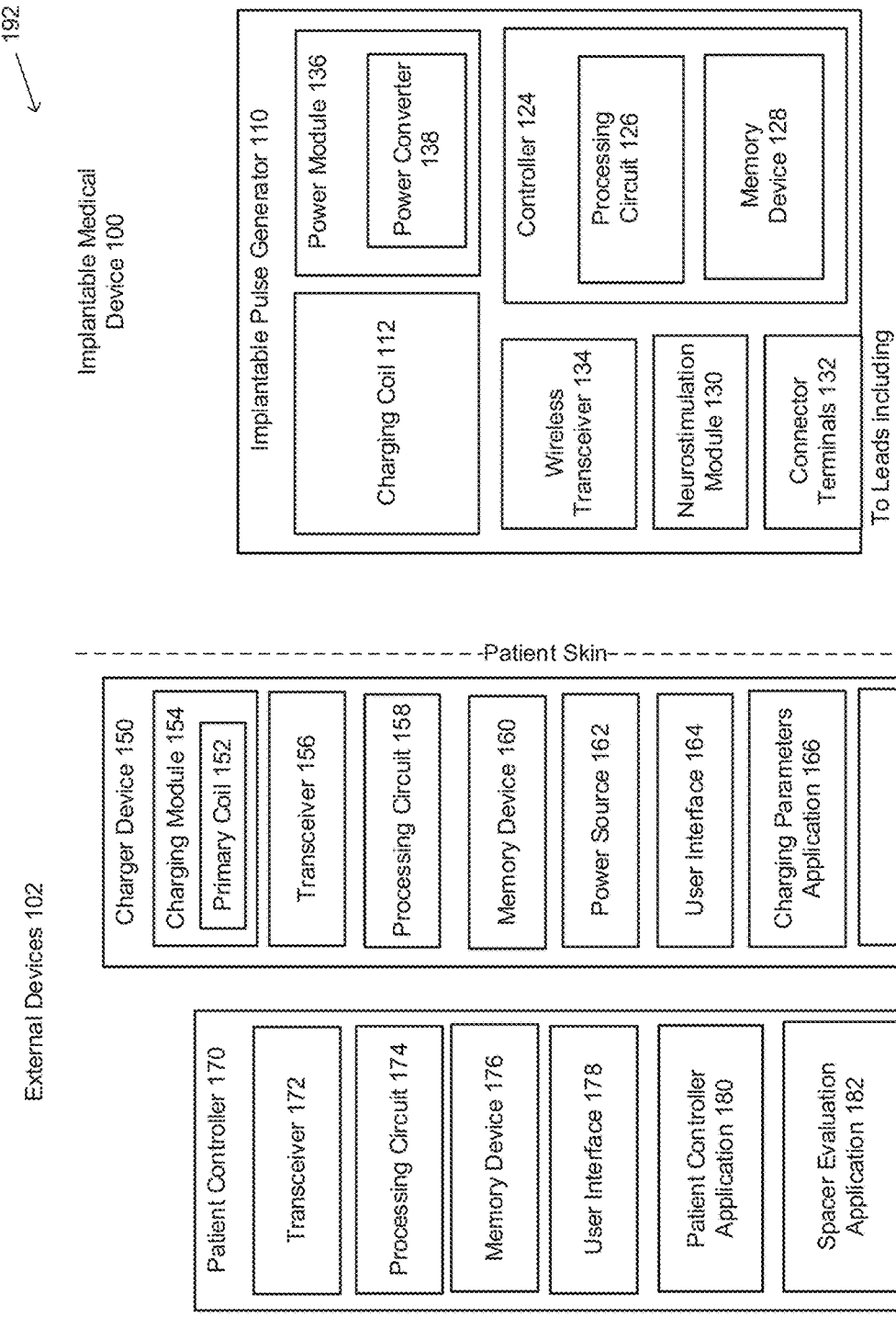
FIG. 1B is a schematic block diagram illustrating an embodiment of selected components of another embodiment of the IMD according to some embodiments.

FIG. 1B is a schematic block diagram illustrating an embodiment of selected components of another embodiment of the IMD 100. The system 192 in FIG. 1B is intended to be exemplary, and in other implementations may include additional or alternative components or devices. In this example, the IMD 100 does not include an internal power source, such as a rechargeable battery. The IMD 100 obtains its power from the charger device 150. For example, the IMD 100 may include a temporary IPG 110 for patient testing or a medical diagnostic device.

The IPG 110 in this example includes a charging coil 112 and a power module 136 with a power converter 138. The power module 136 is operable to receive externally generated power through the charging coil 112. The power convertor 138 converts power from the power module 136 for transfer to one or more components of the IPG 110. The charger device 150 may thus transfer power to the IMD 100 to recharge a battery in the IMD 100 or to power the IMD 100. A sensing circuit 168 in the charger device 150 includes one or more sensors, such as a voltmeter or multimeter, that detects one or more power parameters. The power parameters may include voltage, current or impedance measurements detected from the charging module 154 and/or primary coil 152, such as a bridge current, a bridge voltage or a phase difference between the bridge current and the bridge voltage. In the following description, though recharging a battery 118 in the IMD 100 may be described, a person of skill in the art would understand that the same principles and embodiments would apply to the embodiment in FIG. 1B wherein the charger device 150 provides the power source to the power module 136 of the IMD 100.

When providing power to the IMD 100, the housing of the charger device 150 may directly touch the patient's skin or in other examples, a charger holding device or the patient's clothing may lay between the charger device 150 and the patient's skin. The charger device 150 is moved across the patient's skin to lay above the tissue under which the IPG 110 is implanted. For an efficient inductive coupling, the primary coil 152 and the charging coil 112 should be in alignment with respect to one another, e.g. the primary coil 152 and the charging coil 112 should be within a predetermined distance and have a predetermined position relative to each other. Misalignment of the charger device 150 may introduce unexpected noise, trigger false detection of a presence of the IPG 110, and start false charging. The improper positioning may also lead to inefficient power transfer that causes a longer charging time, high charging power consumption or even generation of heat on undesired metal surfaces of the IMD.

Figure 2A:
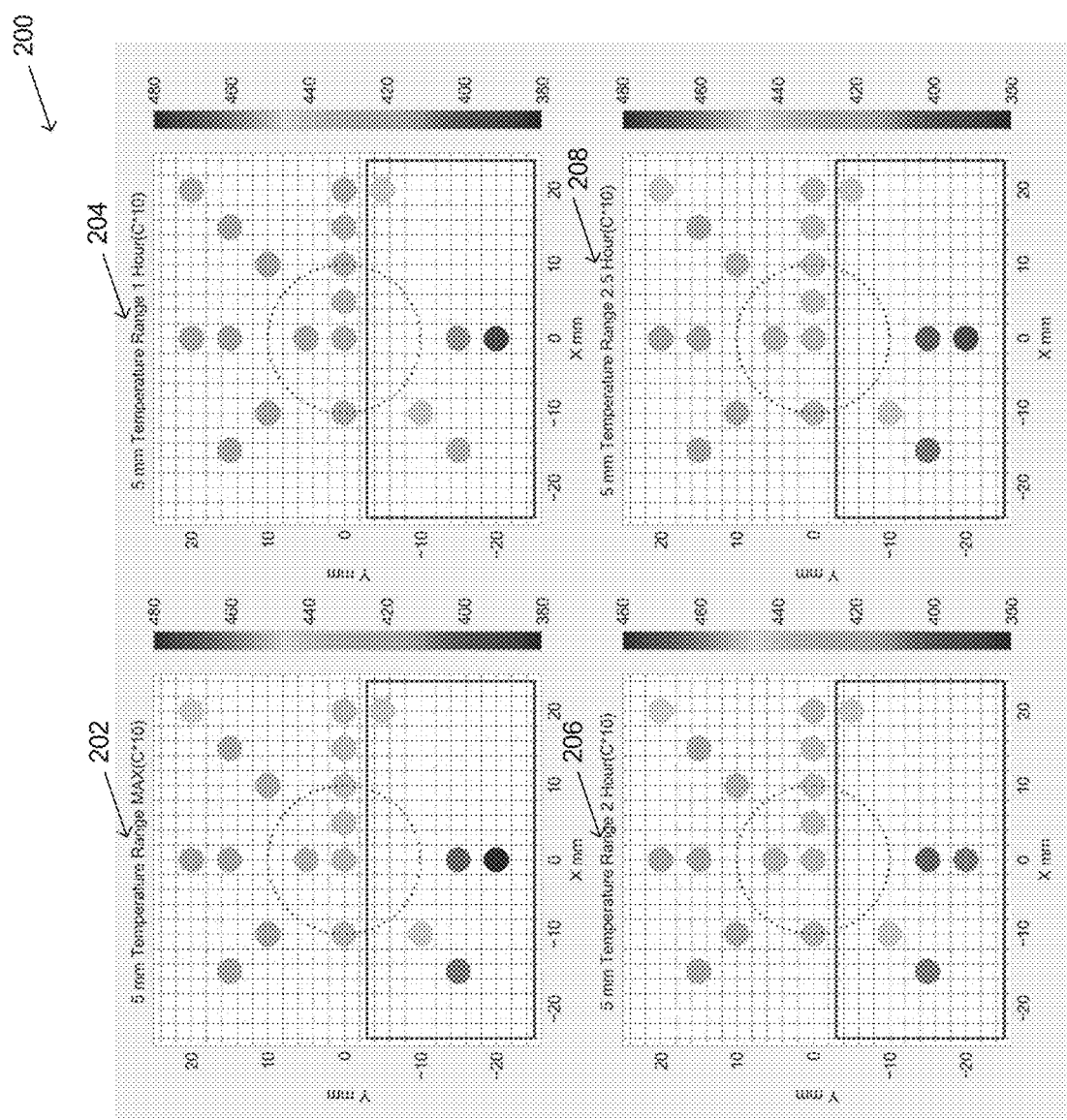
FIGS. 2A, 2B and 2C are graphical representations of temperatures of an IPG during wireless charging at different relative X,Y positions of a charger device and at different charging path depths according to some embodiments.
Figure 2B:
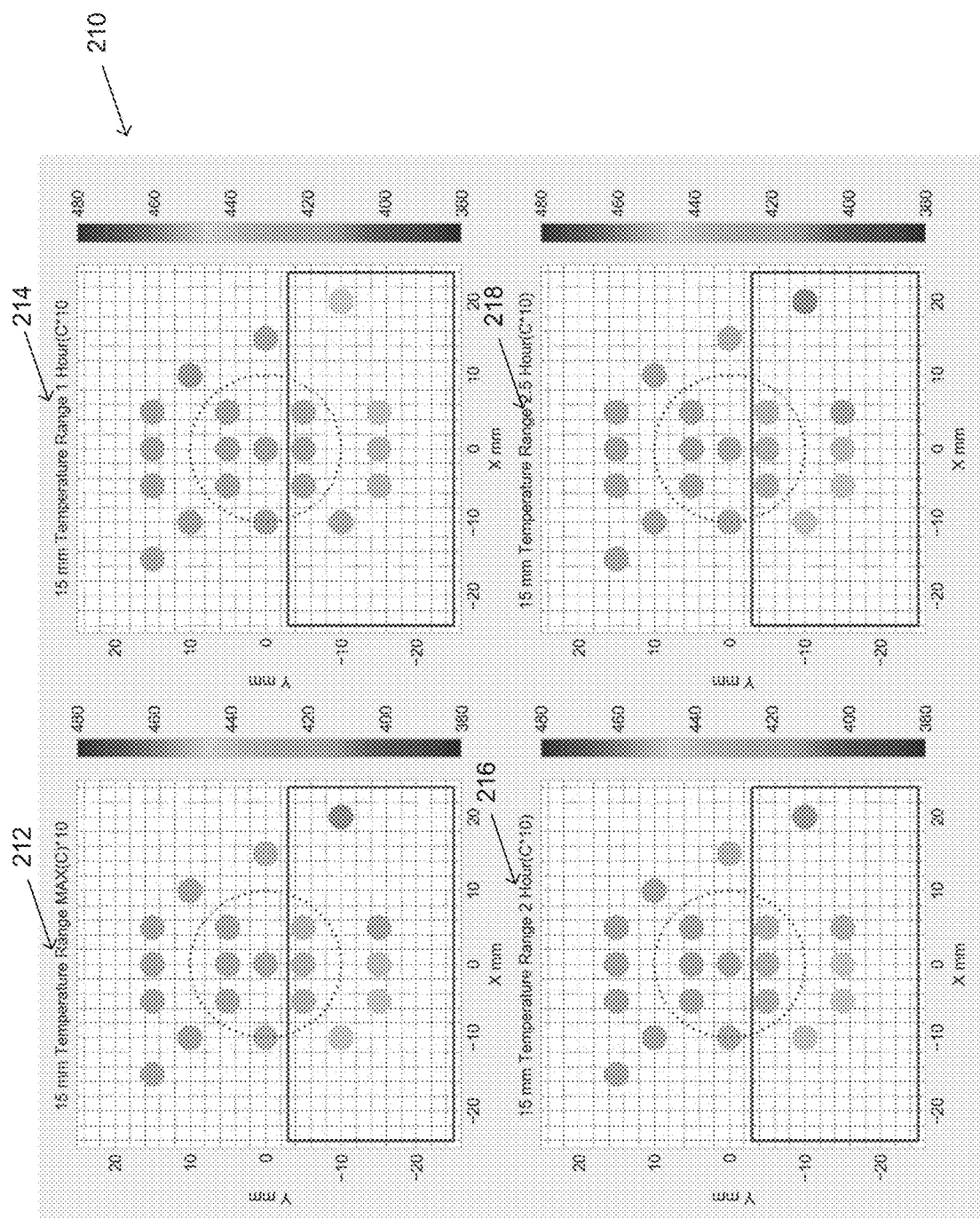
Figure 2C:
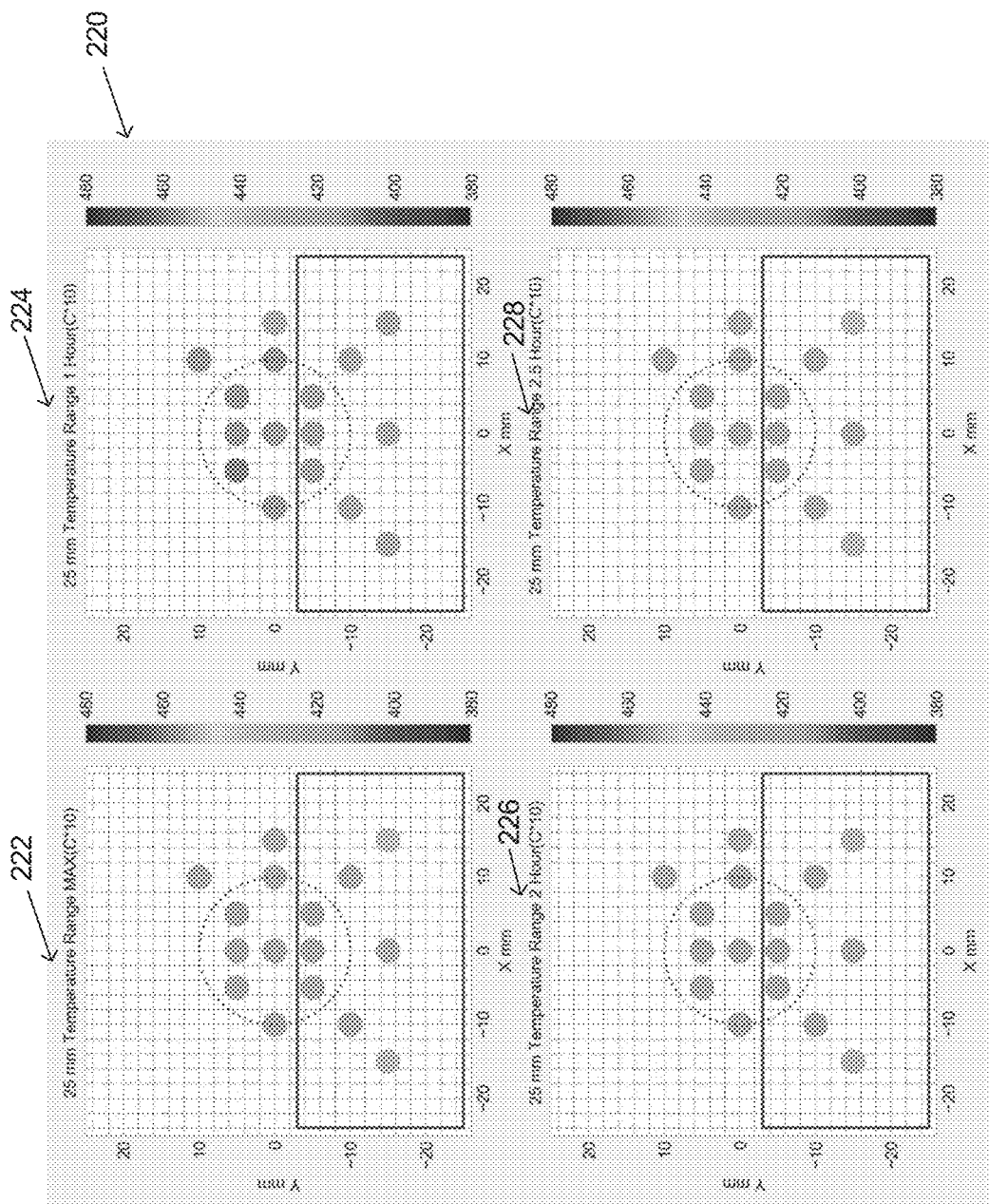

FIGS. 2A, 2B and 2C are graphical representations of temperatures of the IPG 110 during wireless charging at different relative X,Y positions of the charger device 150 and at different charging path depths. During configuration or testing, temperatures of the IPG 110 are measured as the charger device 150 is moved to different relative positions with respect to the IPG 110. For example, FIG. 2A illustrates graphical representations 200 of the temperatures of the IPG 110 at different relative X,Y positions of the charger device 150 with a charging path length of approximately 5 mm. The charging path is the distance between the primary coil 152 in the charger device 150 to the charging coil 112 in the IPG 110. The charger device 150 may have different relative positions to the IPG 110, e.g. in an X,Y plane, as it is slid across the patient's skin. The circles in the X,Y plane represent different relative positions of the charger device 150 from the IPG 110. The IPG 110 is represented as positioned at the center of the graphs at X=0, Y=0.

The temperature of the IPG 110 was measured at the different relative positions of the charger device 150 over time and is represented by the color scale to the right of the graphs. The temperature in the color scale is shown in Celsius multiplied by 10 (C*10). A first graph 202 illustrates the temperature range of the IPG 110 at initiation of power transfer to the IPG 110. A second graph 204 illustrates the temperature range of the IPG 110 after charging for 1 hour. A third graph 206 illustrates the temperature range of the IPG 110 after charging for 2 hours. A fourth graph 208 illustrates the temperature range of the IPG 110 after charging for 2.5 hours. In general, a maximum temperature of 41° C. is desired for comfort and safety of the patient. A temperature of 43° C. after 30 minutes of charging may bring discomfort or tissue damage to the patient. As highlighted by the boxes in each graph, the temperatures are unacceptable for certain positions of the charger device 150 at this distance of 5 mm.

FIG. 2B illustrates graphical representations 210 of the temperatures of the IPG 110 at different relative X,Y positions of the charger device 150 with a charging path of approximately 15 mm. A first graph 212 illustrates the temperature range of the IPG 110 as charging is initiated. A second graph 214 illustrates the temperature range of the IPG 110 after charging for 1 hour. A third graph 216 illustrates the temperature range of the IPG 110 after charging for 2 hours. A fourth graph 218 illustrates the temperature range of the IPG 110 after charging for 2.5 hours. In general, a maximum temperature of 41° C. is desired for comfort and safety of the patient. As seen in the graphs, overall the temperatures are less with this charging path of 15 mm than with the charging path of 5 mm for similar positions of the charger device 150.

FIG. 2C illustrates graphical representations 220 of temperatures of the IPG 110 at different relative X,Y positions of the charger device with a charging path of approximately 25 mm. A first graph 222 illustrates the temperature range of the IPG 110 as charging is initiated. A second graph 224 illustrates the temperature range of the IPG 110 after charging for 1 hour. A third graph 226 illustrates the temperature range of the IPG 110 after charging for 2 hours. A fourth graph 228 illustrates the temperature range of the IPG 110 after charging for 2.5 hours. As seen in the graphs, overall the temperatures are less with this charging path of 25 mm than the charging path of 15 mm and much less than the temperatures with the charging path of 5 mm for similar positions of the charger device 150.

During the energy transfer process that charges the IPG 110, some of the energy may be converted into heat at the charging coil 112 and/or other components of IPG 110. This heat may be referred to as heat loss within IPG 110 during charging. In other words, heat loss may be energy transformed into heat or electrical current dissipated in the resistive loading presented by the coil in the form of heat instead of transformed into electrical current that charges the battery 118. When increased energy levels (e.g., higher power level) are used to charge the battery 118 at a higher rate, the temperature of the IPG 110 may also increase. Although the temperature of the housing of the IPG 110 may not achieve a temperature sufficient to burn or necrose tissue adjacent to the housing of the IPG 110, elevated temperatures may be undesirable and uncomfortable to the patient over time.

For example, a heating threshold may be determined as the maximum cumulative thermal dose identified as still being safe to patient. In other words, the heating threshold may be established or selected to prevent tissue from being heated to an elevated level and duration that could be uncomfortable or undesirable. The heating threshold may be preset by the manufacturer or selected by a clinician. The heating threshold may also be modified over time as needed. In some examples, the heating threshold may not be set to the maximum safe dose. Instead, the heating threshold may be set to a lower value to establish a safety margin below the heating threshold that minimizes potential overheating of tissue.

Components of the IPG 110 in the path between the charger device 150 and the IPG 110 are most prone to heat accumulation during wireless charging. The chances of exceeding a heating threshold increases as the charging path between the charger device 150 and the IPG 110 decreases, e.g., due to the stronger eddy currents generated by the charging magnetic field. Thus, by increasing the charging path from 5 mm to 25 mm, the thermal dose to the IPG 110 was reduced. This reduction in heating is seen across the various positions of the charger device 150 relative to the IPG 110. As such, the temperature of the IPG 110 may be decreased during charging by increasing the charging path.

Figure 3A:
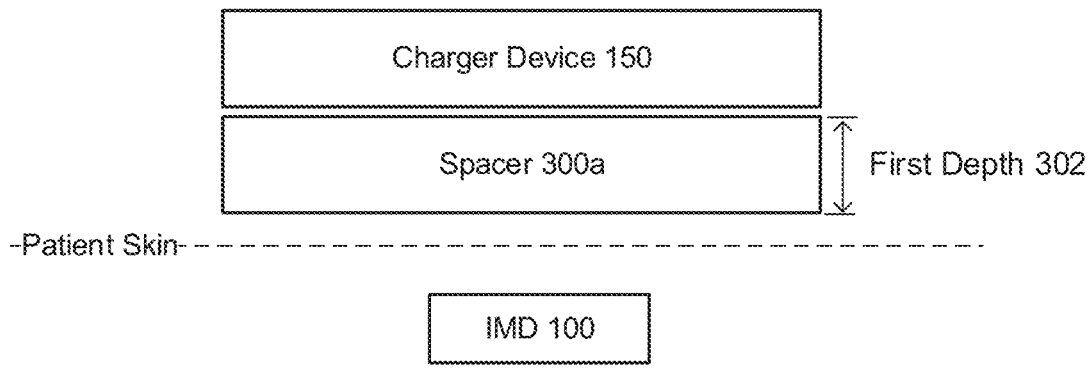
FIGS. 3A, 3B, and 3C are schematic block diagrams of embodiments of one or more spacers 300 positioned between a charger device 150 and patient's skin according to some embodiments.
Figure 3B:
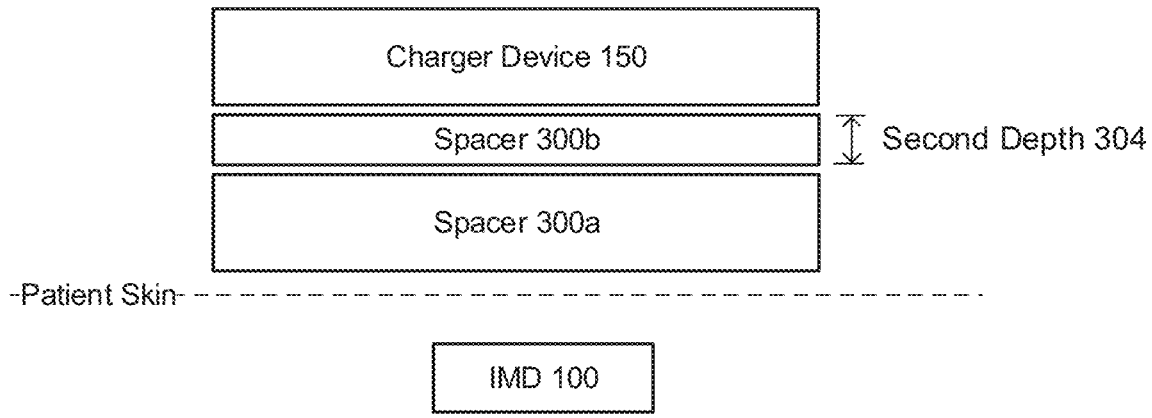
Figure 3C:
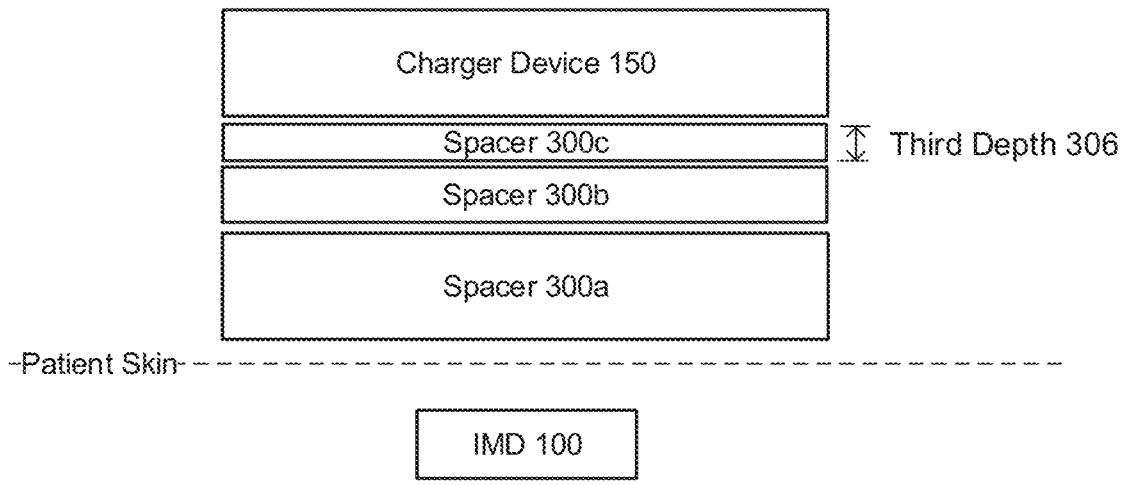

FIGS. 3A, 3B, and 3C are schematic block diagrams of embodiments of one or more spacers 300 positioned between a charger device 150 and patient's skin. In an embodiment, the one or more spacers 300 are positioned between the wireless charger and a patient's skin to increase the length of the charging path to the IMD 100. This increased length in the path helps to reduce heat in components of the IMD 100 subject to the magnetic field of the wireless charger. Since an IMD 100 is generally implanted subcutaneously at depths, depending upon application and type of device, of from 5 mm to 25 mm, the length of the charging path varies between patients. In addition, after implantation, a patient may lose weight or gain weight and thus change the length of the charging path. The spacers 300 may thus be implemented to compensate for these different lengths in the charging paths to prevent unwanted heating.

Each of the spacers 300 are separately attachable to the charger device 150 and are configured to lay between the charger device 150 and a patient's skin. For example, a first side of a spacer 300 is removably attachable to the charger device 150 and a second side of the spacer 300 is removably attachable to another spacer 300. The spacers 300a-c may be attached using clips, slides, glue strips, hook-and-loop fasteners, or other mechanism such that the spacers 300a-c are removably coupled to a charging pad side of the charger device 150 and to other spacers 300. In another example, the spacers 300a-c may be positioned in a holder that secures the charger device 150 to the patient. The spacers 300a-c are made of a low permeability material, such as silicon or plastic, that does not influence the magnetic field generated by the primary coil 152 in the charger device 150.

The spacers 300a-c may selectively increase the length of the charging path between the charger device 150 and IMD 100. The spacers 300a-c are sized with a width and length commensurate with the width and length of the wireless charger device 150 and a relatively uniform depth. Though the width and length are similar among the spacers 300a-c, the spacers 300a-c have different heights or depths. As such, the spacers 300a-c may be used in selected combinations to generate a charging path of different lengths.

For example, FIG. 3A illustrates a schematic block diagram of an embodiment of a first spacer 300a positioned between a charger device 150 and the patient's skin. The first spacer 300a has a relatively uniform first depth 302, e.g., of about 9 mm. The first spacer thus increases the length of the charging path between the charger device 150 and the IMD 100 by at least 9 mm. FIG. 3B illustrates a schematic block diagram of an embodiment of the first spacer 300a and a second spacer 300b positioned between the charger device 150 and the patient's skin. The second spacer 300b has a relatively uniform second depth 304 that is different from the first depth 302 of the first spacer 300a. For example, the second depth may be about 6 mm such that the combination of the first and second spacers creates a depth of 15 mm and thus increases the length of the charging path by at least 15 mm.

FIG. 3C illustrates a schematic block diagram of an embodiment of a first spacer 300a, a second spacer 300b and a third spacer 300c positioned between the charger device 150 and the patient's skin. The third spacer 300c has a relatively uniform third depth 306 that is different from the first depth 302 of the first spacer 300a and different from the second depth 304 of the second spacer 300b. For example, the third depth may be about 3 mm such that the combination of the first, second and third spacers creates a depth of 18 mm. The three spacers 300a-c in this example may thus increase the length of the charging path by 18 mm.

Figure 4:
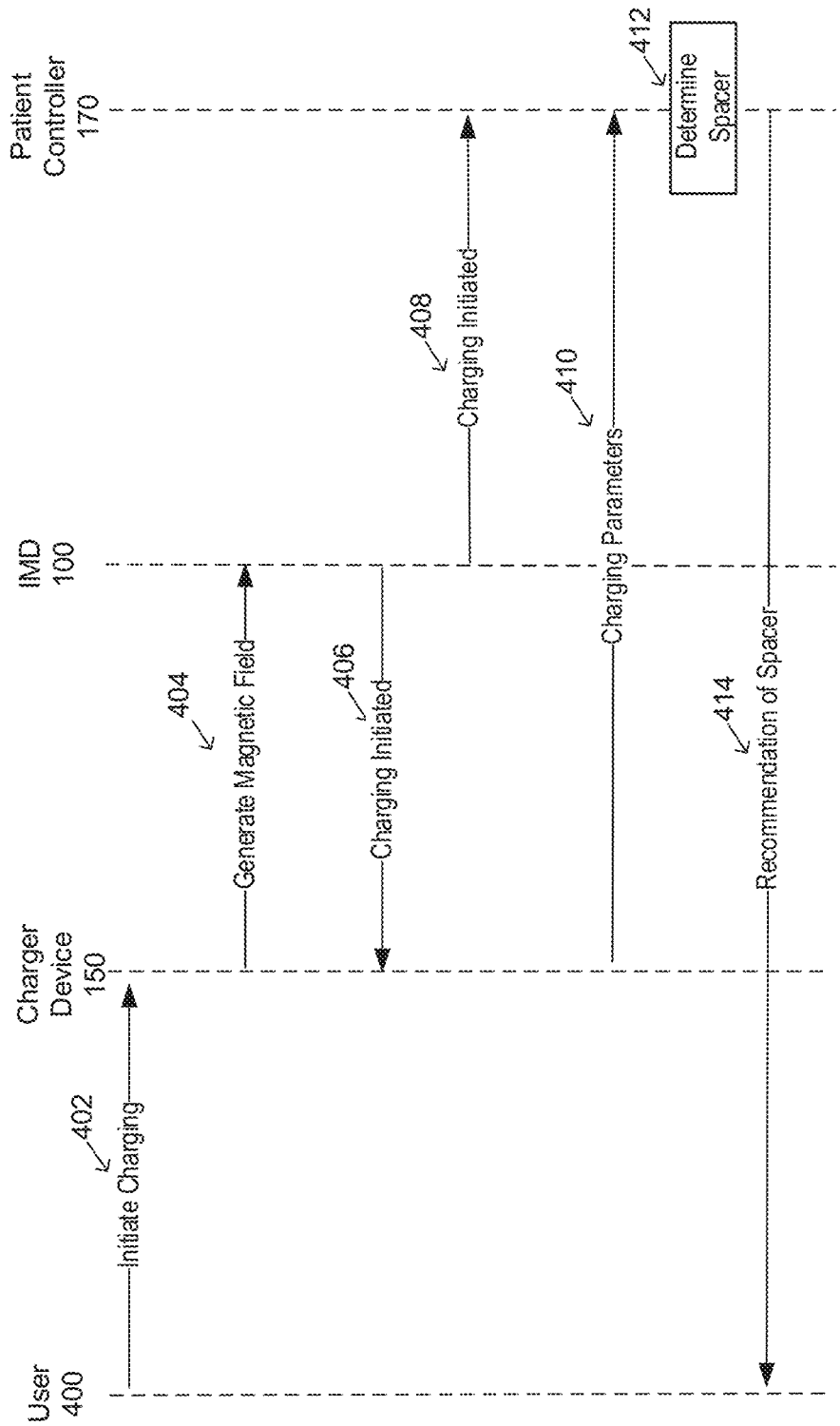
FIG. 4 is a flow diagram of a method for determining whether to implement a spacer according to some embodiments.

FIG. 4 is a flow diagram of an embodiment of a method for determining whether to implement a spacer 300. A user 400 initiates charging of the IMD 100 by the charger device 150 at 402. The charger device 150 initiates charging of the IMD 100 by generating a magnetic field to transfer power from the primary coil 152 to the charging coil 112 at 404. The IMD 100 detects charging has started, e.g. by detecting a current or voltage in the charging coil 112 that indicates charging. The IMD 100 generates and transmits a message, e.g. using near field communication, to the charger device 150 that indicates charging has started at 406. The IMD 100 may also generate a message to the patient controller 170 that indicates charging has started at 408 and transmit the message over an RF frequency using Bluetooth or other wireless protocol.

In an embodiment, the charger device 150 stores power parameters from the charging module 154 and transmits the power parameters to the patient controller 170 at 410. The patient controller 170 analyzes the power parameters and determines whether one or more spacers are needed to prevent undesired heating at 412. The patient controller 170 generates a GUI or other indication to the user of its recommendations at 414. The user 400 may then implement the indicated one or more spacers with the charger device 150.

This process may then be repeated to determine if the one or more spacers have the desired effect of reducing the heating of the IMD 100. The process may also determine whether one or more additional spacers need to be added or whether the depth of the spacers need to be reduced.

In an embodiment, the IMD 100 has limited ability to measure and/or communicate power parameters to the charger device 150 or the patient controller 170. For example, the IMD 100 may be a legacy device that is currently implanted in a patient. Thus, it is not possible to upgrade its hardware without explanting and replacing the IMD 100. The legacy IMD 100 may not have temperature sensors or the circuitry to measure power parameters, such as voltage or current at the recharge module 116. In addition, a legacy IMD may not have the capability to communicate such power parameters to the patient controller 170. Without data from the IMD 100, in an embodiment, the temperature of the IMD 100 must be estimated using the limited data from the charging module 154 of the charger device 150.

Figure 5:
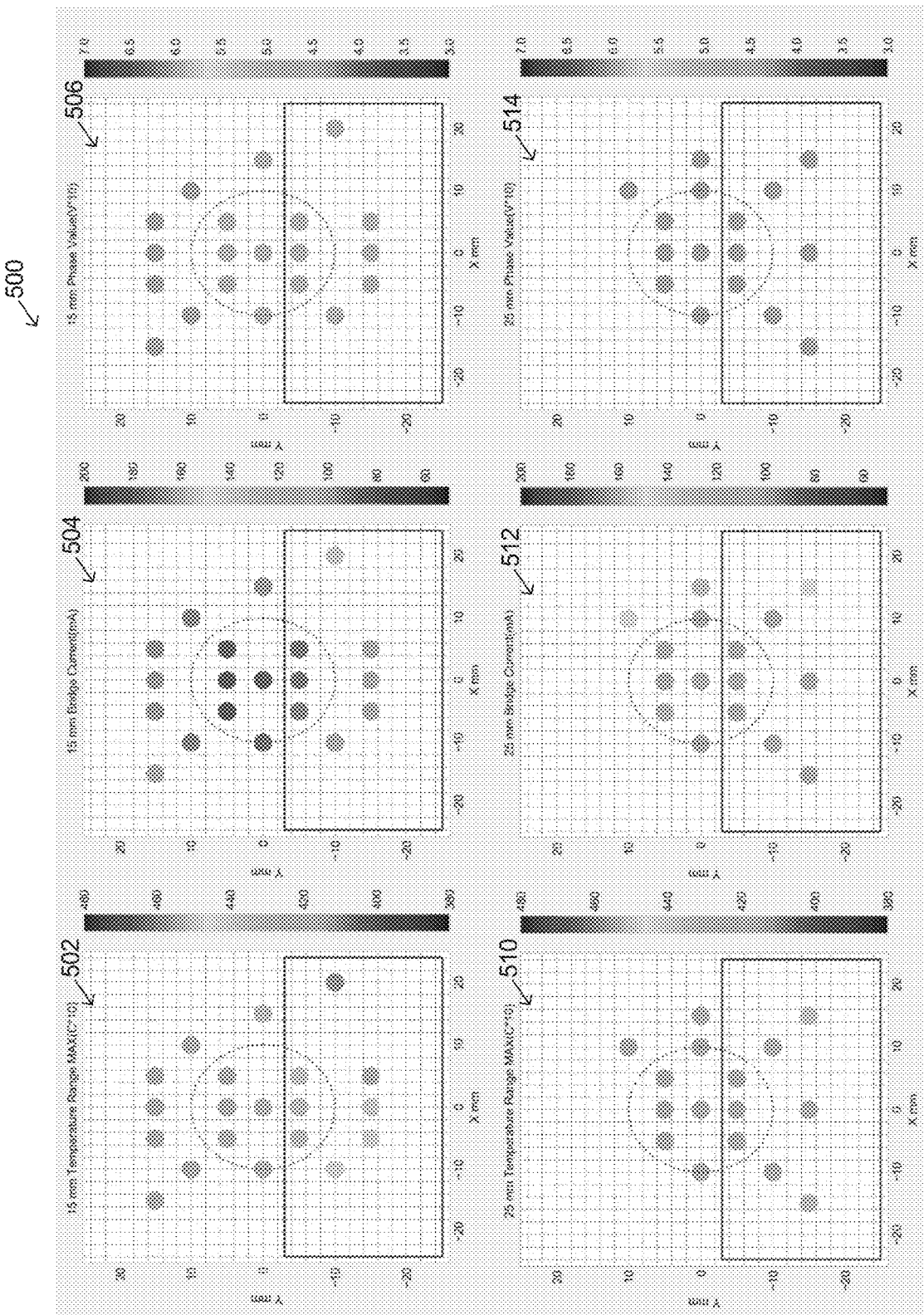
FIG. 5 is a graphical representation of power parameters measured at a charger device and temperature measurements of an IPG according to some embodiments.

FIG. 5 is a graphical representation 500 of power parameters measured at the charger device 150 and corresponding temperature measurements of an IPG 110. During testing or configuration of an IPG 110, various power parameters are measured at the charging module 154 of the charger device 150. Temperatures of the IPG 110 are measured concurrently with the one or more power parameters. A correlation is then determined between the one or more power parameters and temperatures of the IPG 110. During charging, when the IPG 110 is in use, the temperature of the IPG 110 may then be estimated based on one or more of the power parameters.

For example, graph 502 illustrates graphical representations of the temperature of the IPG 110 at different relative X,Y positions of the charger device 150 with a charging path of approximately 15 mm. It is similar to the first graph in FIG. 2B. The bridge current is concurrently measured and depicted in graph 504. A phase value between the bridge current and voltage is also concurrently measured and depicted in graph 506. These power parameters in graph 594 and graph 506 are correlated with the temperature of the IPG 110 for the charging path of 15 mm shown in graph 502. Using this data, a predetermined correlation is determined between a temperature or a range of temperatures of an IPG 110 with values of the power parameters from the charger device 150. In use, the temperature of an implanted IPG 110 may be estimated from the one or more power parameters of the charger device 150 using this predetermined correlation.

In another example, graph 510 illustrates graphical representations of the temperature of the IPG 110 at different relative X,Y positions of the charger device 150 with a charging path of approximately 25 mm. It is similar to the first graph in FIG. 2C. The bridge current of the charger device 150 is concurrently measured and depicted in graph 512. A phase value between the bridge current and voltage of the charger device 150 is also concurrently measured and depicted in graph 514. These power parameters of the bridge current and phase value are correlated with the temperature of the IPG 110 for the charging path of 25 mm. In use, the temperature of an implanted IPG 110 may be estimated from the one or more power parameters of the charger device 150 and this predetermined correlation.

The correlation between the IPG temperature and the power parameters of the charger device 150 is predetermined during configuration and/or testing. The correlation may be mapped directly to the power parameters or mapped to other values determined using the power parameters. For example, the power delivered to the primary coil 152 of the charger device 150 may be calculated by multiplying the current delivered to the primary coil 152 by the voltage delivered to the primary coil 152 and the cosine of the phase angle between the current and voltage waveforms. The power lost in the primary coil 152 may be calculated by multiplying the known impedance of the primary coil 152 by the square of the electrical current of the primary coil 152. So the correlation may be determined between a temperature of the IPG and the power delivered to the primary coil 152 or to a difference of the power delivered to the primary coil 152 and the power lost in the primary coil 152. Other power parameters measured in the charger device 150 or other calculations using these power parameters may be determined as well and correlated with the temperature of the IMD 100.

Figure 6:
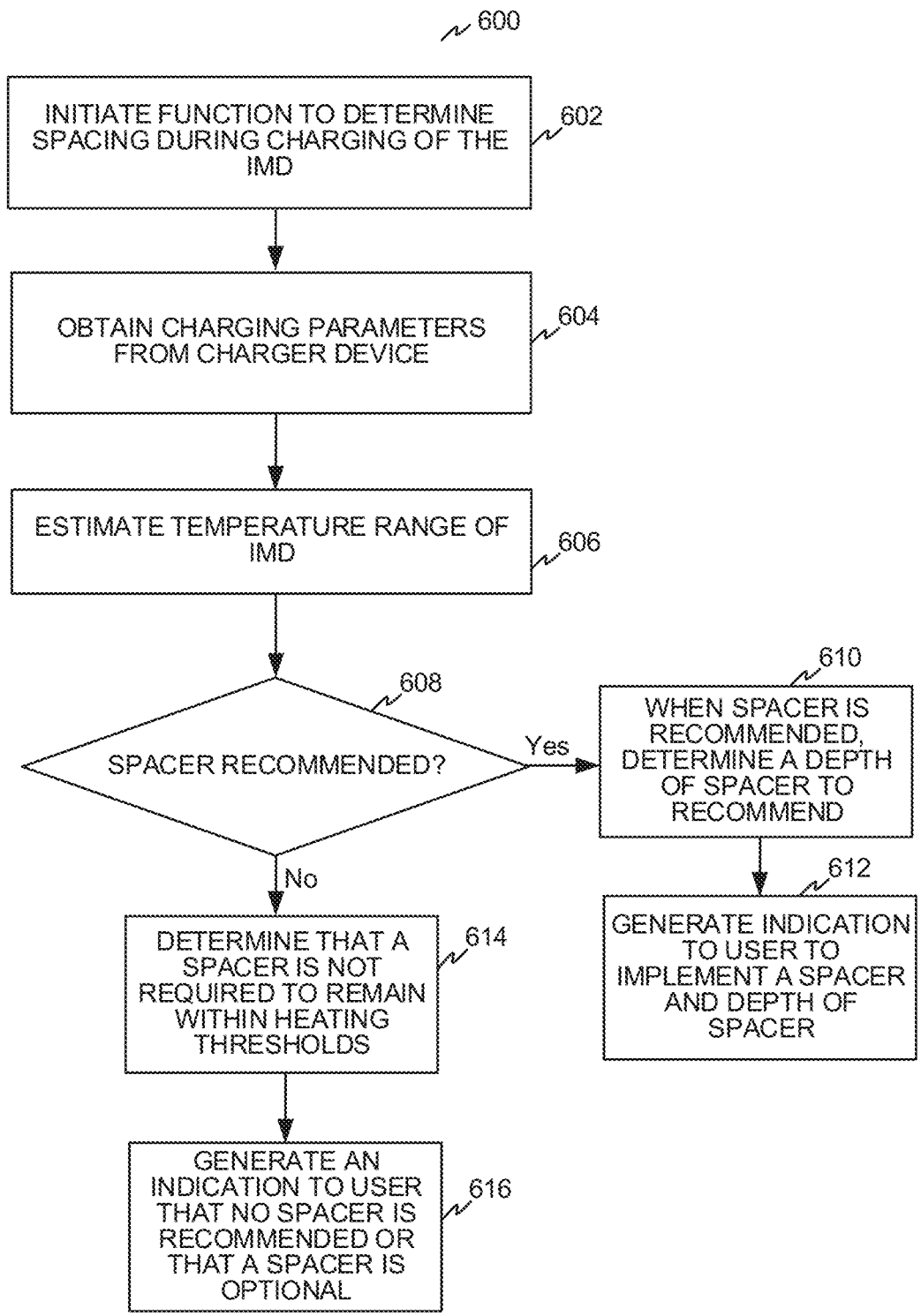
FIG. 6 is a logical flow diagram of an embodiment of a method to determine whether to implement a spacer according to some embodiments.

FIG. 6 is a logical flow diagram of an embodiment of a method 600 to determine whether to implement a spacer. At 602, the function in the patient controller 170 is initiated to determine a need for a spacer. The user may initiate the function or the function may automatically be initiated periodically, such as monthly, during charging of an IMD 100. The function may be implemented in the spacer evaluation application 182 as part of the patient controller application 180 or as a separate function.

The patient controller 170 obtains one or more power parameters from a wireless charger device 150, e.g. when the wireless charger device is charging the IMD at 604. As described above, the power parameters are measured during wireless charging and may include one or more of a bridge current, a bridge voltage, a phase value between the bridge current and the bridge voltage or other measurement by the charger device 150. Using the one or more power parameters, the patient controller 170 estimates a temperature or a temperature range of the IMD 100 at 606. For example, the patient controller 170 correlates the one or more power parameters or a value determined using the power parameters with a temperature range of the IMD 100 using a predetermined correlation. The temperature range is preferably within or less than one degree Celsius. For example, the temperature range may be 41 degrees Celsius to 42 degrees Celsius.

In another embodiment, a neural network or artificial intelligence (AI) processing may be used to correlate the one or more power parameters (or a value determined using the power parameters) with a temperature range of the IMD 100. A training set of known IMD temperatures measured concurrently with one or more power parameters may be used to train and set variables in the AI processor or neural network.

In an embodiment, the patient controller 170 obtains updated power parameters from the charger device 150 periodically, e.g. at 5 minute, 15 minute or 20 minute intervals, and determines the estimated temperature from the power parameters at such intervals. The patient controller 170 first determines the heating of the IMD 100 after a first time interval. Thereafter, the patient controller 170 may determine any incremental heating of the IMD 100 at subsequent time intervals. A heating rate of the IMD 100 may be computed at such subsequent time intervals.

The patient controller 170 then determines whether implementation of a spacer is recommended at 608 using the estimated temperature range of the IMD 100. For example, the estimated temperature range of the IMD 100 may be compared to a heating threshold. The heating threshold may be expressed as the degrees after a predetermined time interval of wireless charging. In one example, the heating threshold may be selected as 43 degrees Celsius after 15 minutes of wireless charging. In another example, the heating threshold may be selected as the equivalent to the IMD 100 at or above 43 degrees Celsius for at least 30 minutes. In other examples, the heating threshold may be selected as one or more of 41 degrees Celsius after 15 minutes of wireless charging, 41.5 degrees after 2 hours of wireless charging or 42 degrees Celsius after 4 hours of wireless charging. When at least one temperature in the estimated temperature range at one or more of the plurality of periodic time intervals exceeds one or more of the heating thresholds, it may be determined that a spacer 300 is recommended at 608.

When a spacer 300 is recommended, the patient controller 170 determines a depth of the spacer to recommend at 610. The depth of the spacer is selectable based on the desired reduction in heating of the IMD 100. For example, one or more spacers may be recommended having a recommended combined depth. The recommended combined depth of the one or more spacers 300 may be determined using the comparison of the estimated temperature range of the IMD 100 and the heating threshold. For example, different, increasing depths of spacers may be recommended when the estimated temperature range exceeds the heating threshold by 5%, 10% or 15%. The patient controller 170 may determine to recommend the depth of the at least one spacer in response to a percentage that the temperature of the IMD 100 exceeds the heating threshold.

In another embodiment, the patient controller 170 may initially recommend a same predetermined depth for each patient, such as a spacer at 5 mm. Such an initial recommendation may then be refined after additional testing.

The patient controller 170 then generates an indication to a user to implement one or more spacers 300 and a combined depth of the one or more spacers at 612. The indication may be a graphical user interface (GUI) on a display, aural or a verbal indication. The patient controller 170 may prevent further charging until a user indicates that the one or more spacers have been implemented, e.g. positioned between the charger device 150 and the patient's skin. The patient controller 170 may reinitiate the function to determine whether the estimated temperature range of the IMD 100 is now within the heating threshold or whether one or more additional spacers are required.

When the estimated temperature range of the IMD 100 is within the heating threshold, the patient controller 170 determines that a spacer is not required at 614. The patient controller 170 then generates an indication to the user that no spacer is needed or that a spacer is optional at 616. For example, even when the estimated temperatures are within the heating thresholds, a user who still feels some discomfort may decide to implement a spacer.

Figure 7:
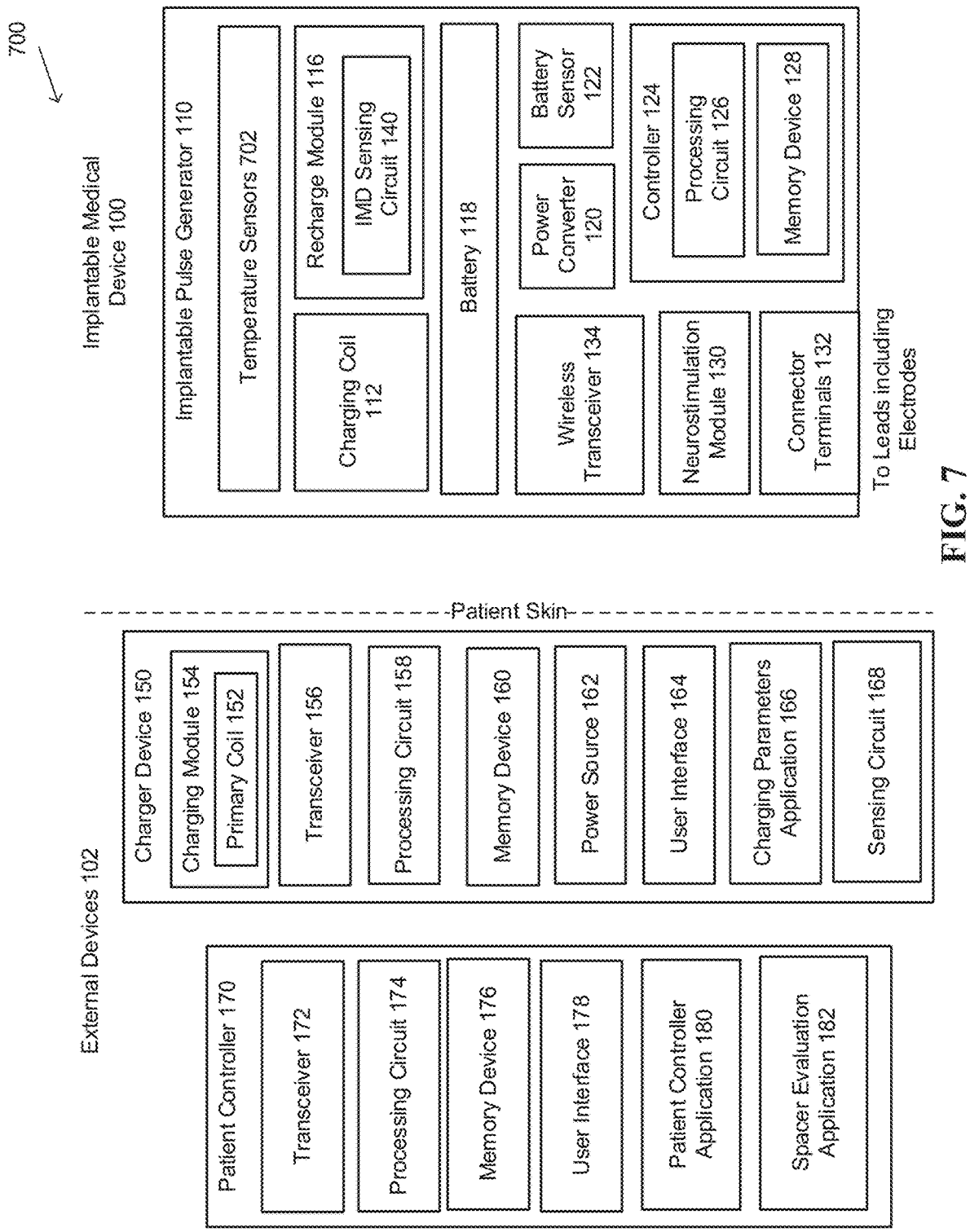
FIG. 7 is a schematic block diagram of another embodiment of an IMD according to some embodiments.

FIG. 7 is a schematic block diagram of another embodiment of an IMD 100. In this exemplary system 700, the IMD 100 is configured to collect and communicate power parameters and/or temperature measurements to the patient controller 170. The IMD 100 in this embodiment includes one or more temperature sensors 702. The temperature sensors 702 may measure one or more of: an internal temperature, a temperature of the housing of the IMD 100, or an external temperature of surrounding tissue. The recharge module 116 may also include IMD sensing circuit 140 that measures the voltage, current or impedance from the charging coil 112, such as a bridge current, a bridge voltage or a phase difference between the bridge current and the bridge voltage. The IMD sensing circuit 140 may include a voltmeter or multimeter. In this embodiment, the IMD 100 is configured to communicate the power parameters and/or temperature measurements to the patient controller 170 using a wireless protocol.

Though the patient controller 170 and the charger device 150 may be shown as separate external devices 102, the functions of the patient controller 170 and the charger device 150 may be implemented in a single external device 102. Alternatively, one or more functions described herein as performed by the patient controller 170 may be implemented in the charger device 150. For example, the spacer evaluation application 182 may be implemented in the charger device 150. The IMD 100 may then communicate the power parameters and/or temperature measurements to the charger device 150 using a wireless protocol.

Figure 8:
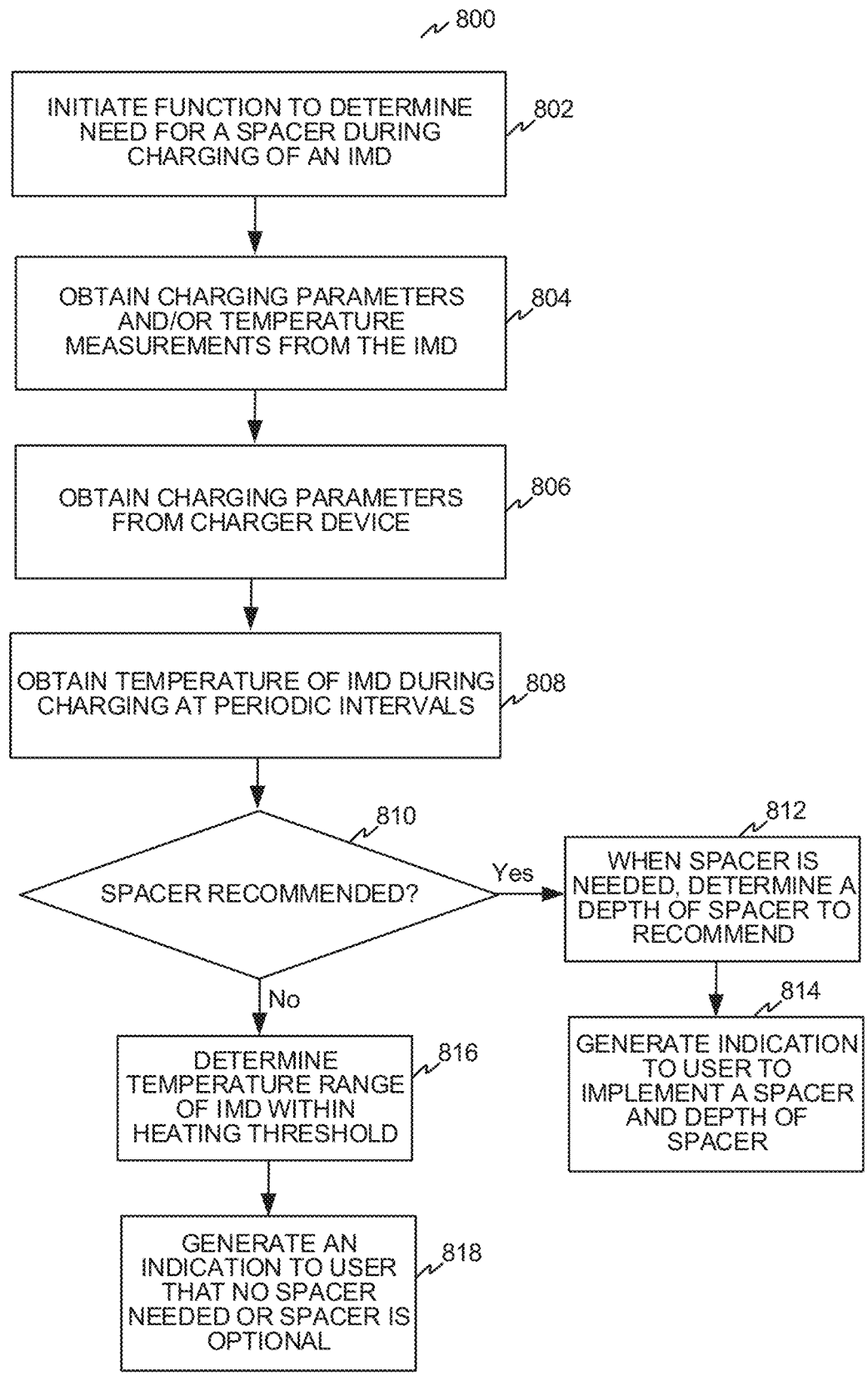
FIG. 8 is a logical flow diagram of an embodiment of a method to determine whether to implement a spacer using parameters from the IMD.

FIG. 8 is a logical flow diagram of an embodiment of a method 800 to determine whether to implement a spacer using parameters from the IMD 100. At 802, the function to determine a need for a spacer is initiated. The user may initiate the function or the function may automatically be initiated periodically, such as monthly upon initiation of charging the IMD 100.

One or more power parameters and/or temperature measurements are obtained from the IMD 100 at 804, wherein the one or more power parameters and/or temperature measurements are measured when the wireless charger device is charging the IMD 100. In an embodiment, one or more power parameters from the charger device 150 may also be obtained at 806. As described above, the power parameters from the charger device 150 may include one or more of bridge current, bridge voltage or phase value between the bridge current and the bridge voltage in the charger device 150. However, these power parameters may not be obtained in some embodiments when the power parameters or temperature measurements from the IMD 100 are obtained.

The temperature or temperature range of the IMD 100 measured during wireless charging is obtained at 808. When temperature measurements are obtained from the IMD 100, then a temperature of the IMD 100 is directly determined. However, if only one or more power parameters are obtained from the IMD 100, a temperature range of the IMD 100 may be estimated by correlating the one or more power parameters with a temperature range of the IMD using a preconstructed table. In another embodiment, a neural network or artificial intelligence (AI) processing may be used to correlate the one or more power parameters from the IMD 100 with a temperature range of the IMD 100. A training set of known IMD temperatures measured at different charging path depths and concurrently measured power parameters is used to train and set variables in the AI or neural network processor.

In an embodiment, the patient controller 170 obtains updated power parameters and/or temperature measurements from the IMD 100 periodically, e.g. at 1 minute, 5 minute, 15 minute or 20 minute intervals. The patient controller 170 may thus determine the heating of the IMD 100 after a first time interval. Thereafter, the patient controller 170 may determine any incremental heating of the IMD 100 at subsequent time intervals.

It is then determined whether implementation of a spacer 300 is recommended at 810 by comparing a temperature (or estimated temperature range) of the IMD at the periodic time intervals with one or more heating thresholds. The one or more heating thresholds may be expressed as the degrees after a predetermined time interval of wireless charging. In one example, the heating threshold may be selected as 43 degrees Celsius after 15 minutes of wireless charging. In another example, the heating threshold may be selected as the equivalent to the IMD 100 at or above 43 degrees Celsius for at least 30 minutes. In other examples, the heating threshold may be selected as one or more of 41 degrees Celsius after 15 minutes of wireless charging, 41.5 degrees after 2 hours of wireless charging or 42 degrees Celsius after 4 hours of wireless charging. When at least one temperature measurement at one or more of the plurality of periodic intervals exceeds one or more of the heating thresholds, it may be determined that a spacer 300 is recommended.

When a spacer 300 is needed, a depth of the required spacer is determined at 812. For example, spacers 300 may be provided at various depths, such as from 1-10 mm. For example, one or more spacers 300 may be recommended having a recommended combined depth. The recommended combined depth of the one or more spacers 300 may be determined using the comparison of the estimated temperature range of the IMD 100 and the heating threshold. For example, different, increasing depths of spacers 300 may be recommended when the estimated temperature range exceeds the heating threshold by 5%, 10% or 15%. The patient controller 170 may thus determine to recommend the depth of the at least one spacer in response to a difference or percentage that the temperature of the IMD exceeds the heating threshold.

In another embodiment, the patient controller 170 may initially recommend a same predetermined depth for each patient, such as a spacer at 5 mm. Such an initial recommendation may then be refined after additional testing.

In general, for efficient inductive coupling (higher values of k), it is preferred that the charging path is minimized. The charging path is the distance between the charger device 150 and the IMD 100 along the Z axis perpendicular to a centerline of the center plane of the wire windings of the primary coil 152 and/or charging coil 112. This charging path may not be completely eliminated since the charger device 150 is generally placed on the patient's skin, and the IMD 100 has been implanted at a particular depth within the tissue of the patient. However, when the distance Z is minimized, unwanted heating of the IMD 100 may occur. Thus, a balance must be obtained between preventing unwanted heating and efficient inductive coupling. This balance may require lengthening the distance Z, e.g. the charging path, to prevent unwanted heating using the one or more spacers 300. However, a charging path of too great a length results in longer charging times due to lower power transfer efficiency. Such longer charging times are inconvenient to a patient and may result in under charging of the IMD 100. Thus, a balance must be determined between power transfer, amount of time required for charging and prevention of unwanted heating.

The higher the efficiency of energy transfer, the more energy can be transferred while at the same time limiting the heating of surrounding components and tissue. The length of the charging path in an embodiment should be determined to be a minimum to prevent unwanted heating but allow efficient energy transfer in a convenient amount of time. The patient controller 170 may thus determine a minimum depth of the at least one spacer 300 to reduce heating to a safe threshold and so maintain efficient energy transfer. The efficiency of the power transfer may be calculated and used in the determination of the depth of the spacer 300.

An indication to implement a spacer 300 and of a depth of the spacer 300 is then generated to the user at 814. The indication may be a graphical user interface (GUI) on a display, aural or a verbal indication. Further charging may be halted until the user indicates that the spacer 300 is implemented. The function may be repeated to determine whether the temperature of the IMD 100 is now within the heating threshold or whether an additional spacer is necessary.

When the temperature of the IMD 100 is within the heating threshold at 816, the spacer 300 is not recommended. An indication to the user that no spacer 300 is required or that a spacer 300 is optional is generated at 818.

Figure 9A:
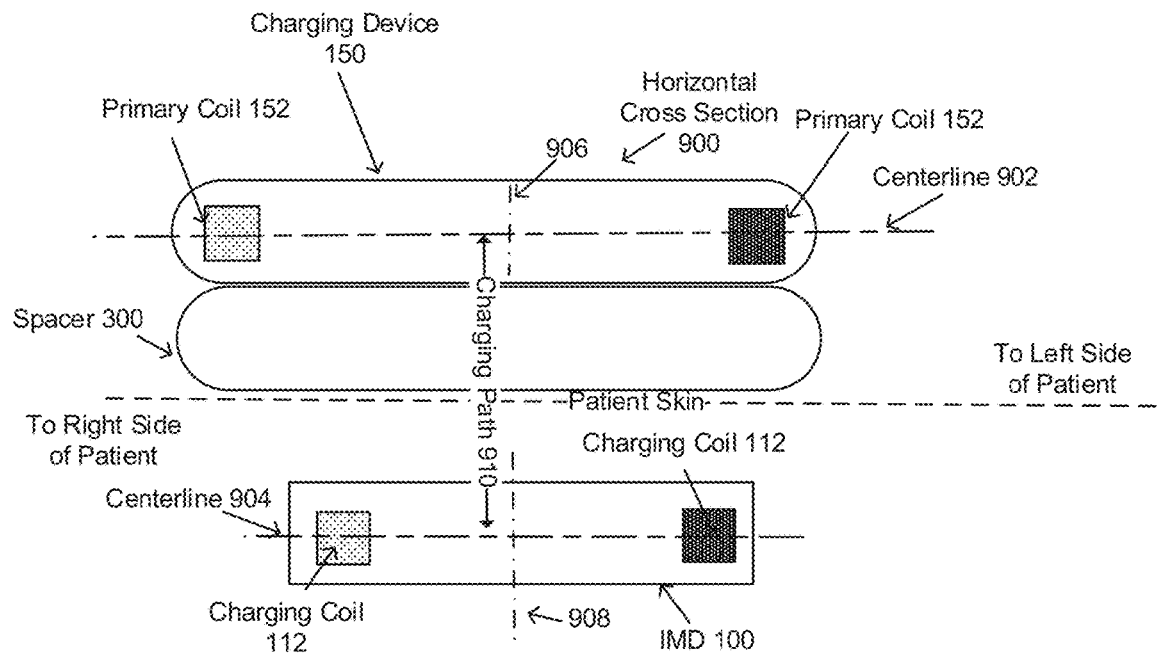
FIG. 9A is a schematic block diagram of a horizontal cross section of the charger device and a cross section of the IMD that are aligned according to some embodiments.

FIG. 9A illustrates a horizontal cross section 900 of a charger device 150 and a cross section of the IMD 100 that are aligned. The horizontal cross section 900 of the charger device 150 shows a centerline 902 of a center plane of the wire windings of the primary coil 152 and a central axis 906 of the wire windings of the primary coil 152. Moreover, in this example, a central axis 908 of the wire windings of the charging coil 112 in the IMD 100 is shown and a centerline 904 of a center plane of the wire windings of the charging coil 112 of the IMD 100. For efficient inductive coupling (higher values of k), it is preferred that the coils are axially aligned, e.g. the axes 906 and 908 are collinear and parallel. In this embodiment, the charger device 150 and the IMD 100 are aligned. The spacer 300 is positioned between the charger device 150 and the patient's skin and increases charging path 910 by a length of approximately the depth of the spacer 300.

Figure 9B:
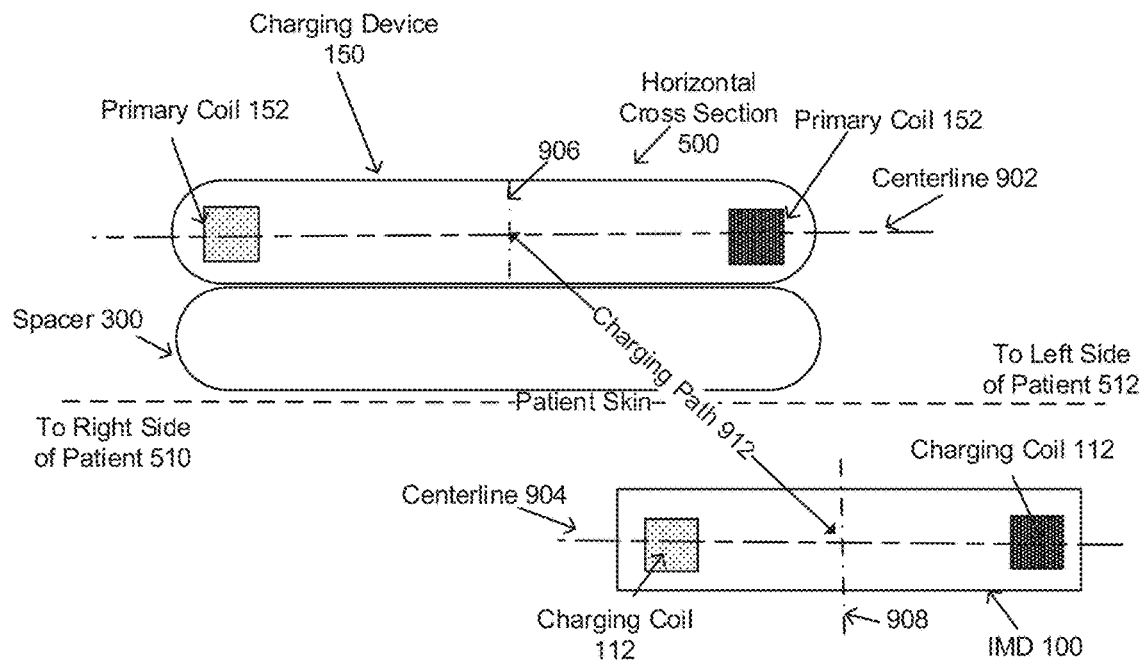
FIG. 9B is a schematic block diagram of a horizontal cross section of the charger device and a cross section of the IMD that are not aligned according to some embodiments.

FIG. 9B illustrates a horizontal cross section 900 of the charger device 150 and a cross section of the IMD 100 that are not aligned. In this example, the charger device 150 has been moved more towards the left side of the patient from that shown in FIG. 9A such that axes 906 and 908 around which the primary coil 152 and the charging coil 112 are wound are no longer collinear and parallel. For example, the user may move or position the charger device 150 with the attached spacer 300 to this position that is not axially aligned.

The spacer 300 is still positioned between the charger device 150 and the patient's skin. Though the charger device 150 and the IMD 100 are not aligned, the spacer 300 still increases the charging path 912. Thus, the spacer 300 increases the length of the charging path when the charger device 150 and IMD are aligned and also when not aligned.

Figure 10:
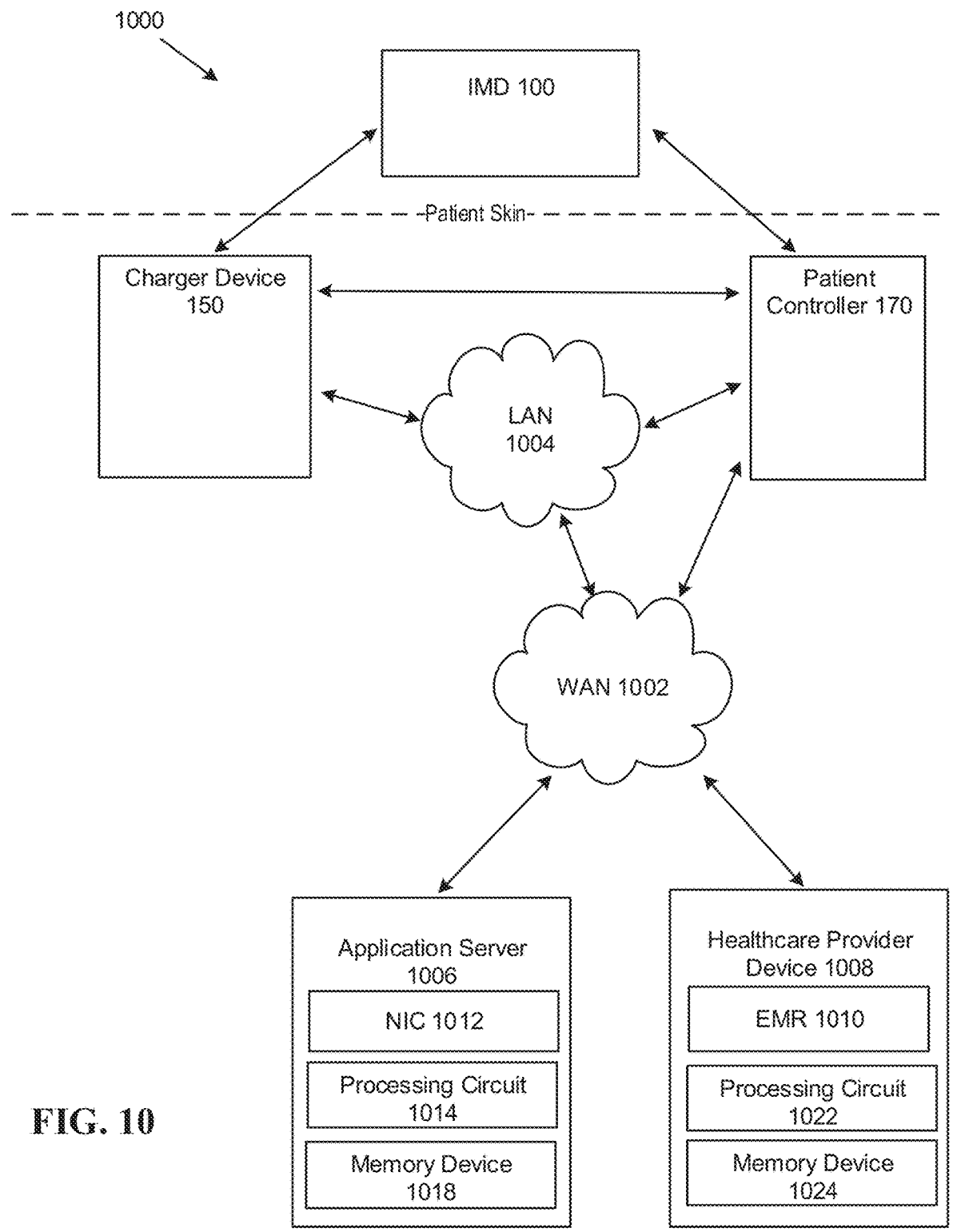
FIG. 10 is a schematic block diagram of an exemplary network in which the charger device and the patient controller may operate according to some embodiments.

FIG. 10 is a schematic block diagram of an exemplary network 1000 in which the charger device 150 and patient controller 170 may operate. The exemplary network 1000 includes one or more networks that are communicatively coupled, e.g., such as a wide area network (WAN) 1002 and a local area network (LAN) 1004. The WAN 1002 may include a wireless or wired WAN, such as a 4G or 5G cellular network, service provider network, Internet, etc. The LAN 1004 may include a wired or wireless LAN and operate inside a home or enterprise environment. Other networks may be included to communicatively couple the devices, such as edge networks, metropolitan area networks, satellite networks, etc.

The IMD 100 may communicate using a wireless protocol to one or more of the charger device 150 or the patient controller 170. The patient controller 170 and the charger device 150 may communicate directly using Bluetooth or other wireless or wired protocol or communicate indirectly through the WLAN. Though the charger device 150 and the patient controller 170 are shown as separate devices, the charger device 150 may be incorporated into the patient controller 170. The patient controller 170 and/or the charger device 150 may be implemented in a user device, such as a smart phone, laptop, desktop, smart tablet, smart watch, or other electronic device.

In an embodiment, the charger device 150 and/or patient controller 170 may communicate to an application server 1006. The application server 1006 may provide software updates to the charger device 150 and/or the patient controller 170. The charger device 150 and/or the patient controller 170 may provide operational data and/or patient data to the application server 1006. The application server 1006 includes a network interface circuit 1012 and a server processing circuit 1014. The network interface circuit (NIC) 1012 includes an interface for wireless and/or wired network communications with one or more of the exemplary networks in the network 1600. The NIC 1012 may also include authentication capability that provides authentication prior to allowing access to some or all of the resources of the application server 1006. The NIC 1012 may also include firewall, gateway, and proxy server functions. The application server 1006 also includes a processing circuit 1014 and a memory device 1018. For example, the memory device 1018 is a non-transitory, processor readable medium that stores instructions and/or data which when executed or processed by the processing circuit 1014, causes the application server 1006 to perform one or more functions described herein.

In another embodiment, the charger device 150 and/or patient controller 170 may communicate to a local or remote healthcare provider device 1008, e.g. in a physician's office, clinic, or hospital. The healthcare provider device 1008 may store patient or therapeutic information in an electronic medical record (EMR) 1010 associated with the user of the IMD 100. The healthcare provider device 1008 also includes a processing circuit 1022 and a memory device 1024. For example, the memory device 1024 is a non-transitory, processor readable medium that stores instructions and/or data which when executed by the processing circuit 1022, causes the healthcare provider device 1008 to perform one or more functions described herein.

Figure 11:
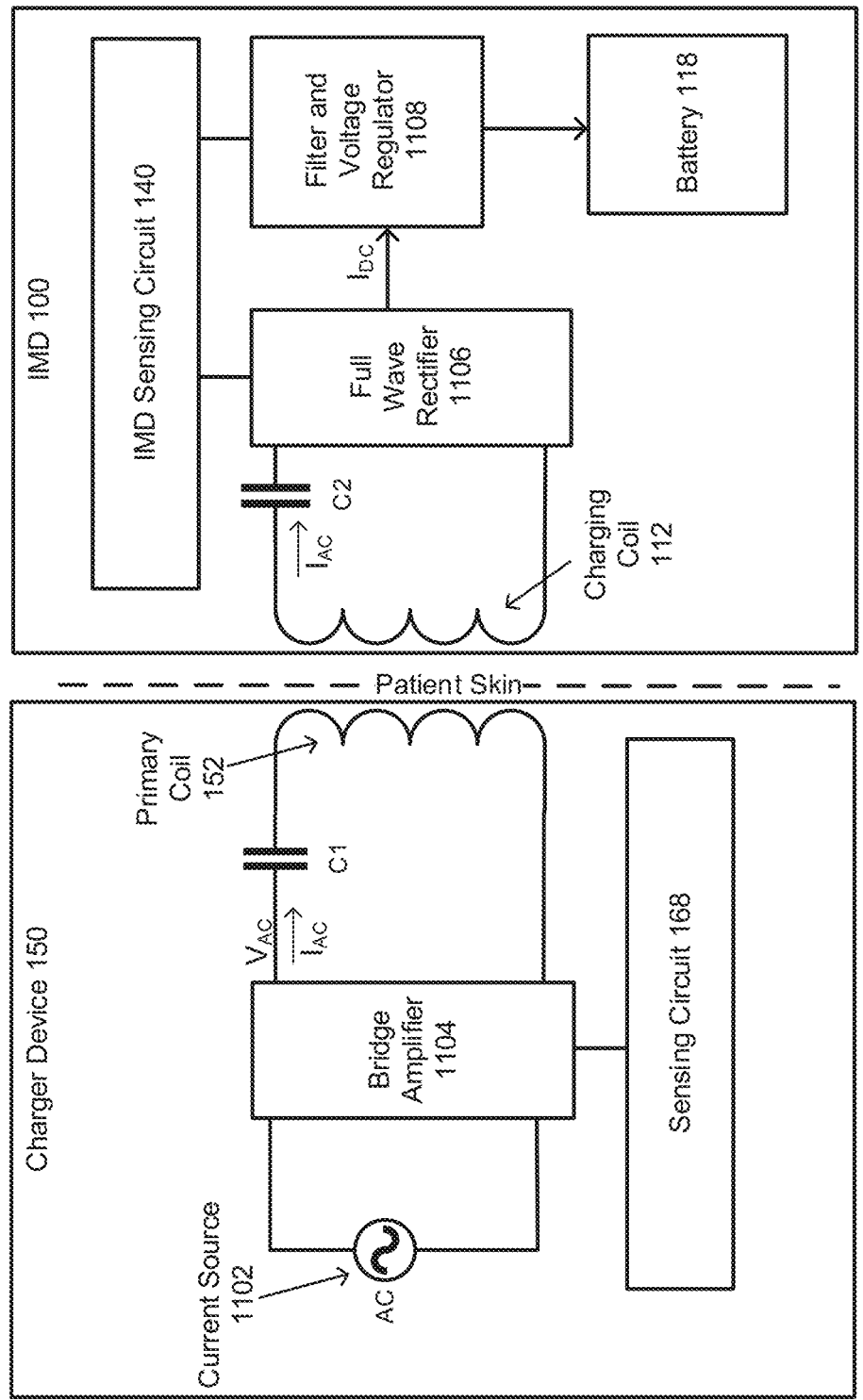
FIG. 11 is a schematic block diagram of a wireless power transmitter in the charger device and a wireless power receiver in the IMD according to some embodiments.

FIG. 11 is a schematic block diagram of an embodiment of the wireless power transmitter and receiver. The charger device 150 includes an oscillator or AC current source 1102 that outputs an AC current at a resonant frequency. A bridge amplifier 1104 serves as an amplifier for driving the primary coil 152. The bridge current $I_{AC}$ and/or bridge voltage $V_{AC}$ output from the bridge current may be included as power parameters from the charger device 150. In addition, a phase difference between the bridge current $I_{AC}$ and the bridge voltage $V_{AC}$ may also be included as a power parameter from the charger device 150. The sensing circuit 168 includes one or more sensors, such as a voltmeter or multimeter, that detects these power parameters.

The fluctuating magnetic field generated by the primary coil generates an alternating current $I_{AC}$ in the charging coil 112. A full wave rectifier 1106 converts the incoming AC current $I_{AC}$ to a direct current $I_{DC}$. A filter and voltage regulator 1108 create a useable voltage for charging the battery 118. The incoming AC current $I_{AC}$, voltage or the direct current $I_{DC}$ may be included as power parameters from the IMD 100. The IMD sensing circuit 140 includes one or more sensors, such as a voltmeter or multimeter, that detects these power parameters.

A processing circuit as described herein includes one or more processing devices on one or more printed circuit boards, including one or more of a microprocessor, microcontroller, digital signal processor, video graphics processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory device is a non-transitory memory device and may be an internal memory or an external memory to the processing circuit, and the memory may be a single memory device or a plurality of memory devices. The memory device may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects have been described with reference to specific examples. Various modifications and changes may be made, however, without departing from the scope as set forth in the claims. The specification and figures are illustrative, rather than restrictive, and modifications are intended to be included within the scope of the claims. Accordingly, the scope of the claims should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition, or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present embodiments, in addition to those not specifically recited, may be varied, or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

The invention claimed is:

1. An external device, comprising:
   a transceiver configured to communicate with a wireless charger device, wherein the wireless charger device is configured to provide energy to an implantable medical device (IMD);
   at least one processing circuit including at least one processing device and at least one memory device, wherein the at least one memory device stores instructions that, when executed by the at least one processing device, causes the external device to:
      obtain one or more power parameters detected by a sensing circuit in the charger device;
      estimate a temperature range of the IMD using the one or more power parameters from the charger device; and
      determine to recommend coupling at least one spacer to the charger device using the estimated temperature range of the IMD.

2. The external device of claim 1, wherein the at least one memory device stores instructions that when executed by the at least one processing device, causes the external device to:
   compare the temperature range of the IMD to at least one heating threshold.

3. The external device of claim 2, wherein the at least one memory device stores instructions that when executed by the at least one processing device, causes the external device to:
   when the temperature range of the IMD exceeds the at least one heating threshold, determine to recommend coupling the at least one spacer to the charger device, wherein the at least one spacer is configured to be removably coupled to the charger device in a position to lay adjacent to a charging pad of the charger device and face a patient's skin.

4. The external device of claim 3, wherein the at least one memory device stores instructions that when executed by the at least one processing device, causes the external device to:
   determine a depth of the at least one spacer in response to the comparison of the temperature range of the IMD and the heating threshold.

5. The external device of claim 4, wherein the at least one memory device stores instructions that when executed by the at least one processing device, causes the external device to:
   determine the depth of the at least one spacer in response to a percentage that the temperature range of the IMD exceeds the heating threshold.

6. The external device of claim 2, wherein the at least one memory device stores instructions that when executed by the at least one processing device, causes the external device to:
   when the temperature range of the IMD is within the heating threshold, generate an indication to a user that a spacer is optional.

7. The external device of claim 1, wherein the one or more power parameters obtained from the charger device include one or more of: a bridge current, a bridge voltage or a phase difference between the bridge current and the bridge voltage.

8. The external device of claim 1, wherein the at least one memory device stores instructions that when executed by the at least one processing device, causes the external device to:
   determine the temperature range of the IMD using a predetermined correlation.

9. A user device, comprising:
   a transceiver configured to communicate with an external wireless charger device, wherein the wireless charger device is configured to provide energy to an implantable medical device (IMD);
   at least one processing circuit including at least one processing device and at least one memory device, wherein the at least one memory device stores instructions that, when executed by the at least one processing device, causes the user device to:
      obtain one or more power parameters detected by the wireless charger device;
      estimate a temperature range of the IMD using the one or more power parameters detected by the wireless charger device; and
      generate a recommendation to couple at least one spacer to the wireless charger device using the estimated temperature range of the IMD.

10. The user device of claim 9, wherein the at least one memory device stores instructions that when executed by the at least one processing device, causes the user device to:

determine whether the temperature range of the IMD exceeds one or more heating thresholds; and when the temperature range of the IMD exceeds the one or more heating thresholds, generate the recommendation to couple at least one spacer to the wireless charger device, wherein the at least one spacer is removably coupled to the wireless charger device in a position to lay adjacent to a charging pad of the wireless charger device and face a patient's skin.

11. The user device of claim 10, wherein the at least one memory device stores instructions that when executed by the at least one processing device, causes the user device to:

determine a recommended depth of the at least one spacer in response to the comparison of the temperature range of the IMD and the one or more heating thresholds; and wherein the recommendation includes the recommended depth.

12. The user device of claim 10, wherein the at least one memory device stores instructions that when executed by the at least one processing device, causes the user device to:

determine a recommended depth of the at least one spacer in response to a percentage that the temperature range of the IMD exceeds the one or more heating thresholds; and wherein the recommendation includes the recommended depth.

13. The user device of claim 9, wherein the at least one memory device stores instructions that when executed by the at least one processing device, causes the user device to:

when the temperature range of the IMD is within the one or more heating thresholds, generate an indication that a spacer is optional.

14. The user device of claim 9, wherein the one or more power parameters detected by the wireless charger device include one or more of: a bridge current, a bridge voltage, or a phase difference between the bridge current and the bridge voltage.

15. The user device of claim 14, wherein the at least one memory device stores instructions that when executed by the at least one processing device, causes the user device to:

determine the temperature range of the IMD using a predetermined correlation between values of the one or more power parameters and temperature ranges of the IMD.

16. A user device, comprising:

a transceiver configured to communicate with an external wireless charger device, wherein the wireless charger device is configured to provide energy to an implantable medical device (IMD);

at least one processing circuit including at least one processing device and at least one memory device, wherein the at least one memory device stores instructions that, when executed by the at least one processing device, causes the user device to:

obtain one or more power parameters detected by the wireless charger device;

access a predetermined correlation between values of the one or more power parameters and temperature ranges of the IMD;

determine an estimated temperature range of the IMD using the one or more power parameters and the predetermined correlation; and determine whether the estimated temperature range of the IMD exceeds one or more heating thresholds; and when the estimated temperature range of the IMD exceeds the one or more heating thresholds, generate a recommendation to couple at least one spacer to the wireless charger device.

17. The user device of claim 16, wherein the at least one spacer is removably coupled to the wireless charger device in a position to lay adjacent to a charging pad of the wireless charger device and face a patient's skin.

18. The user device of claim 17, wherein the at least one memory device stores instructions that when executed by the at least one processing device, causes the user device to:

determine a recommended depth of the at least one spacer in response to the comparison of the estimated temperature range of the IMD and the one or more heating thresholds; and wherein the recommendation includes the recommended depth of the at least one spacer.

19. The user device of claim 18, wherein the at least one memory device stores instructions that when executed by the at least one processing device, causes the user device to:

when the estimated temperature range of the IMD is within the one or more heating thresholds, generate an indication that a spacer is optional.

20. The user device of claim 16, wherein the one or more power parameters detected by the wireless charger device include one or more of: a bridge current, a bridge voltage, or a phase difference between the bridge current and the bridge voltage.

* * * * *